(12) United States Patent
    Calabro et al.

(10) Patent No.: US 9,012,395 B2
(45) Date of Patent: Apr. 21, 2015

(54) TREATMENT OF EXTRACELLULAR MATRIX TO REDUCE INFLAMMATION

(71) Applicant: The Cleveland Clinic Foundation, Cleveland, OH (US)

(72) Inventors: Anthony Calabro, Cleveland Heights, OH (US); Mark Lauer, Olmsted Falls, OH (US); Vincent Hascall, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/159,129

(22) Filed: Jan. 20, 2014

(65) Prior Publication Data

US 2014/0135256 A1 May 15, 2014

Related U.S. Application Data

(63) Continuation of application No. 13/489,974, filed on Jun. 6, 2012, now Pat. No. 8,658,593.

(60) Provisional application No. 61/520,173, filed on Jun. 6, 2011.

(51) Int. Cl.
    *A61K 38/17* (2006.01)
    *A61K 31/70* (2006.01)
    *A61K 31/7008* (2006.01)
    *A61K 31/728* (2006.01)
    *A61K 38/19* (2006.01)

(52) U.S. Cl.
    CPC ........... *A61K 31/728* (2013.01); *A61K 38/1709* (2013.01); *A61K 38/191* (2013.01)

(58) Field of Classification Search
    None
    See application file for complete search history.

(56) References Cited

U.S. PATENT DOCUMENTS

| | | |
|---|---|---|
| 5,310,881 A | 5/1994 | Sakurai et al. |
| 6,444,447 B1 | 9/2002 | DeAngelis |
| 6,982,298 B2 | 1/2006 | Calabro et al. |
| 7,223,571 B2 | 5/2007 | DeAngelis et al. |
| 7,368,502 B2 | 5/2008 | Calabro et al. |
| 7,465,766 B2 | 12/2008 | Calabro et al. |
| 7,741,091 B2 | 6/2010 | DeAngelis et al. |
| 7,884,087 B1 | 2/2011 | Bellini et al. |
| 8,021,350 B2 | 9/2011 | Calabro et al. |
| 8,080,260 B2 | 12/2011 | Derwin et al. |
| 8,137,688 B2 | 3/2012 | Zahos et al. |
| 8,138,265 B2 | 3/2012 | Calabro et al. |
| 8,207,262 B2 | 6/2012 | Calabro et al. |
| 2002/0192280 A1 | 12/2002 | Hunter et al. |
| 2003/0171332 A1* | 9/2003 | Abraham et al. ............. 514/54 |
| 2009/0170195 A1 | 7/2009 | Basu et al. |
| 2010/0227402 A1 | 9/2010 | Carter et al. |
| 2012/0083445 A1* | 4/2012 | Tseng et al. ............. 514/13.3 |

FOREIGN PATENT DOCUMENTS

WO    00/44367 A2    8/2000

OTHER PUBLICATIONS

Milner et al., TSG-6: a pluripotent inflammatory mediator?, Biochem Soc. Transaction, (2006) vol. 34, part 3, pp. 446-450.*
Forteza and Salathe, Chapter 15, Hyaluronan in the Airways, from Chemistry and Biology of Hyaluronan, Garg & Hales, Eds., pp. 323-337, 2004.*
Zhuo L, Kanamori A, Kannagi R, Itano N, Wu J, Hamaguchi M, et al, "SHAP potentiates the CD44-mediated leukocyte adhesion to the hyaluronan substratum," J Biol Chem, Jul. 21, 2006, 281(29), 20303-20314.
Al'Qteishat A, Gaffney J, Krupinski J, Rubio F, West D, Kumar S, et al, "Changes in hyaluronan production and metabolism following ischaemic stroke in man," Brain, 2006, 129(Pt 8), 2158-2176.
Aytekin M, Comhair SA, De La Motte C, Bandyopadhyay SK, Farver CF, Hascall VC, et al, "High levels of hyaluronan in idiopathic pulmonary arterial hypertension," Am J Physiol Lung Cell Mol Physiol, Nov. 2008, 295(5), L789-L799.
Bárdos T, Kamath RV, Mikecz K, Glant TT, "Anti-Inflammatory and chondroprotective effect of TSG-6 (tumor necrosis factor-α-stimulated gene-6) in murine models of experimental arthritis," Am J Pathol, Nov. 2001, 159(5), 1711-1721.
Blundell et al, "The Link Module from Ovulation- and Inflammation-associated Protein TSG-6 Changes Conformation on Hyalauronan Binding," Jl. of Biol. Chem, 278:49, pp. 49261-49270 (2003).
Brown TJ, Laurent UB, Fraser JR, "Turnover of hyaluronan in synovial joints: elimination of labelled hyaluronan from the knee joint of the rabbit," Exp Physiol, 1991, 76(1), 125-134.
Calabro A, Benavides M, Tammi M, Hascall VC, Midura RJ, "Microanalysis of enzyme digests of hyaluronan and chondroitin/dermatan sulfate by fluorophore-assisted carbohydrate electrophoresis (FACE)," Glycobiology, 2000, 10(3), 273-281.

(Continued)

*Primary Examiner* — Karlheinz R Skowronek
*Assistant Examiner* — Joseph Fischer
(74) *Attorney, Agent, or Firm* — Pearne & Gordon LLP

(57) ABSTRACT

Pharmaceutical compositions are provided. The compositions comprise a compound comprising the hyaluronan-containing structure A-(low molecular weight hyaluronan domain)-B. The compositions also comprise a pharmaceutically acceptable excipient. A is hydrogen, a substituent that does not comprise a binding site for tumor necrosis factor stimulated gene-6 ("TSG-6") protein, a substituent that interferes with binding of TSG-6 protein immediately adjacent thereto, or chondroitin. B is hydroxyl, a substituent that does not comprise a binding site for TSG-6 protein, a substituent that interferes with binding of TSG-6 protein immediately adjacent thereto, or chondroitin. The composition is suitable for administration by injection, inhalation, topical rub, or ingestion. Also disclosed are methods and kits for treating a site of inflammation in an individual in need thereof and for decreasing heavy chain modification of pathological hyaluronan at a site of inflammation in an individual in need thereof based on administering the compounds or the compositions.

5 Claims, 21 Drawing Sheets

(56) References Cited

OTHER PUBLICATIONS

Castor CW, Prince RK, Hazelton MJ, "Hyaluronic acid in human synovial effusions; a sensitive indicator of altered connective tissue cell function during inflammation," Arthritis Rheum, Dec. 1966, 9(6), 783-794.

Choi H, Lee RH, Bazhanov N, Oh JY, Prockop DJ, "Anti-Inflammatory protein TSG-6 secreted by activated MSCs attenuates zymosan-induced mouse peritonitis by decreasing TLR2/NF-κB signaling in resident macrophages," Blood, Jul. 14, 2011, 118(2), 330-338.

Coleman PJ, Scott D, Mason RM, Levick JR, "Role of hyaluronan chain length in buffering interstitial flow across synovium in rabbits," J Physiol, 2000, 526(Pt 2), 425-434.

Coleman PJ, Scott D, Ray J, Mason RM, Levick JR, "Hyaluronan secretion into the synovial cavity of rabbit knees and comparison with albumin turnover," J Physiol, 1997, 503(Pt 3), 645-656.

De La Motte CA, Hascall VC, Calabro A, Yen-Lieberman B, Strong SA, "Mononuclear leukocytes preferentially bind via CD44 to hyaluronan on human intestinal mucosal smooth muscle cells after virus infection or treatment with poly(I.C)," J Biol Chem, Oct. 22, 1999, 274(43), 30747-30755.

De La Motte CA, Hascall VC, Drazba J, Bandyopadhyay SK, Strong SA, "Mononuclear leukocytes bind to specific hyaluronan structures on colon mucosal smooth muscle cells treated with polyinosinic acid:polycytidylic acid: inter-α-trypsin inhibitor is crucial to structure and function," Am J Pathol, Jul. 2003; 163(1), 121-133.

Decker B, McGuckin WF, McKenzie BF, Slocumb CH, "Concentration of hyaluronic acid in synovial fluid," Clin Chem, 1959, 5(5), 465-469.

Forteza R, Casalino-Matsuda SM, Monzon ME, Fries E, Rugg MS, Milner CM, et al, "TSG-6 potentiates the antitissue kallikrein activity of inter-α-inhibitor through bikunin release," Am J Respir Cell Mol Biol, 2007, 36, 20-31.

Fraser JR, Kimpton WG, Pierscionek BK, Cahill RN, "The kinetics of hyaluronan in normal and acutely inflamed synovial joints: observations with experimental arthritis in sheep," Semin Arthritis Rheum, Jun. 1993, 22(6 Suppl 1), 9-17.

Fraser JR, Laurent TC, "Turnover and metabolism of hyaluronan," Ciba Found Symp, 1989,143, 41-59 and 281-285.

Fries E, Kaczmarczyk A, "Inter-α-inhibitor, hyaluronan and inflammation," Acta Biochim Pol, 2003, 50(3), 735-742.

Fülöp C, Szántó S, Mukhopadhyay D, Bárdos T, Kamath RV, Rugg MS, et al, "Impaired cumulus mucification and female sterility in tumor necrosis factor-induced protein-6 deficient mice," Development, 2003, 130(10), 2253-2261.

Getting SJ, Mahoney DJ, Cao T, Rugg MS, Fries E, Milner CM, et al, "The link module from human TSG-6 inhibits neutrophil migration in a hyaluronan- and inter-α-inhibitor-independent manner," J Biol Chem, Dec. 27, 2002, 277(52), 51068-51076.

Glant TT, Finnegan A, Mikecz K, "Proteoglycan-induced arthritis: immune regulation, cellular mechanisms, and genetics," Crit Rev Immunol, 2003, 23(3), 199-250.

Glant TT, Kamath RV, Bárdos T, Gál I, Szántó S, Murad, YM, et al, Cartilage-specific constitutive expression of TSG-6 protein (product of tumor necrosis factor α-stimulated gene 6) provides a chondroprotective, but not anti-inflammatory, effect in antigen-induced arthritis, Arthritis Rheum, Aug. 2002, 46(8), 2207-2218.

Hascall VC, Laurent TC, "Hyaluronan: structure and physical properties," In: Science of Hyaluronan Today, Hascall VC, Yanagishita M eds, Seikagaku Corp., Tokyo, Japan; 1997; http://glycoforum.gr.jp/science/hyaluronan/HA01/HA01E.html.

Huang L, Yoneda M, Kimata K, "A serum-derived hyaluronan-associated protein (SHAP) is the heavy chain of the inter-α-trypsin inhibitor," J Biol Chem, Dec. 15, 1993, 268(35), 26725-26730.

International Search Report and Written Opinion issued Jan. 29, 2013 in corresponding PCT Patent Application No. PCT/US2012/041066.

Jessen TE, Ødum L, "Role of tumour necrosis factor stimulated gene 6 (TSG-6) in the coupling of inter-α-trypsin inhibitor to hyaluronan in human follicular fluid" Reproduction, 2003, 125(1), 27-31.

Kahmann, J.D. et al, "Localization and characterization of the hyaluronan-binding site on the Link module from human TSG-6," Structure, 2000, 8(7), 763-774.

Kida D, Yoneda M, Miyaura S, Ishimaru T, Yoshida Y, Ito T, et al, "The SHAP-HA complex in sera from patients with rheumatoid arthritis and osteoarthritis," J Rheumatol, 1999, 26(6), 1230-1238.

Kim KS, Park SJ, Yang JA, Jeon JH, Bhang SH, Kim BS, et al, "Injectable hyaluronic acid-tyramine hydrogels for the treatment of rheumatoid arthritis," Acta Biomater, Feb. 2011, 7(2), 666-674.

Lauer ME, Mukhopadhyay D, Fulop C, De La Motte CA, Majors AK, Hascall VC, "Primary murine airway smooth muscle cells exposed to poly(I,C) or tunicamycin synthesize a leukocyte-adhesive hyaluronan matrix," J Biol Chem, Feb. 20, 2009, 284(8), 5299-5312.

Levick JR, McDonald JN, "Fluid movement across synovium in healthy joints: role of synovial fluid macromolecules," Ann Rheum Dis, 1995, 54(5), 417-423.

Lindenhayn K, Heilmann HH, Niederhausen T, Walther HU, Pohlenz K, "Elimination of tritium-labelled hyaluronic acid from normal and osteoarthritic rabbit knee joints." Eur J Clin Chem Clin Biochem, 1997, 35(5), 355-363.

Milner CM, Tongsoongnoen W, Rugg MS, Day AJ, "The molecular basis of inter-α-inhibitor heavy chain transfer on to hyaluronan," Biochem Soc Trans, 2007, 35(Pt 4), 672-676.

Mindrescu C, Thorbecke GJ, Klein MJ, Vilček J, Wisniewski HG, "Amelioration of collagen-induced arthritis in DBA/1J mice by recombinant TSG-6, a tumor necrosis factor/interleukin-1-induced protein," Arthritis Rheum, Dec. 2000, 43(12), 2668-2677.

Mukhopadhyay D, Asari A, Rugg MS, Day AJ, Fülöp C, "Specificity of the tumor necrosis factor-induced protein 6-mediated heavy chain transfer from inter-α-trypsin inhibitor to hyaluronan: implications for the assembly of the cumulus extracellular matrix." J Biol Chem, Mar. 19, 2004, 279(12), 11119-11128.

Mukhopadhyay D, Hascall VC, Day AJ, Salustri A, Fülöp C, "Two distinct populations of tumor necrosis factor-stimulated gene-6 protein in the extracellular matrix of expanded mouse cumulus cell-oocyte complexes," Arch Biochem Biophys, Oct. 15, 2001, 394(2), 173-181.

Oh JY, Roddy GW, Choi H, Lee RH, Ylöstalo JH, Rosa, Jr RH, et al, "Anti-inflammatory protein TSG-6 reduces inflammatory damage to the cornea following chemical and mechanical injury," PNAS, Sep. 28, 2010, 107 (39), 16875-16880.

Rees, M.D. et al., "Hypochlorite-Mediated Fragmentation of Hyaluronan, Chondroitin Sulfates, and Related N-Acetyl Glycosamines: Evidence for Chloramide Intermediates, Free Radical Transfer Reactions, and Site-Specific Fragmentation," J Am Chem Soc, 2003, 125(45), 13719-13733.

Rugg MS, Willis AC, Mukhopadhyay D, Hascall VC, Fries E, Fülöp C, et al, "Characterization of complexes formed between TSG-6 and inter-α-inhibitor that act as intermediates in the covalent transfer of heavy chain onto hyaluronan," J Biol Chem, Jul. 8, 2005, 280(27), 25674-25686.

Sandson J, Hamerman D, Schwick G, "Altered properties of pathological hyaluronate due to a bound inter-alpha trypsin inhibitor," Trans Assoc Am Physicians, 1965, 78, 304-313.

Sanggaard KW, Scavenius C, Rasmussen AJ, Wisniewski HG, Thøgersen IB, Enghild JJ, "The TSG-6/HC2-mediated transfer is a dynamic process shuffling heavy chains between glycosaminoglycans," J Biol Chem, Jul. 16, 2010, 285(29), 21988-21993.

Shen L, Zhuo L, Okumura A, Ishikawa T, Miyachi M, Owa Y, et al, "The SHAP-hyaluronan complex in serum from patients with chronic liver diseases caused by hepatitis virus infection," Hepatology Research, 2006, 34,178-186

Stern R, Kogan G, Jedrzejas MJ, Šoltés L, "The many ways to cleave hyaluronan," Biotechnol Adv, 2007, 25(6), 537-557.

Szántó S, Bárdos T, Gál I, Glant TT, Mikecz K, "Enhanced neutrophil extravasation and rapid progression of proteoglycan-induced arthritis in TSG-6-knockout mice," Arthritis Rheum, Sep. 2004, 50(9), 3012-3022.

Wisniewski HG, Burgess WH, Oppenheim JD, Vilček J, "TSG-6, an arthritis-associated hyaluronan binding protein, forms a stable complex with the serum protein inter-α-inhibitor," Biochemistry, Jun. 14, 1994, 33(23), 7423-7429.

(56) References Cited

OTHER PUBLICATIONS

Wisniewski HG, Hua JC, Poppers DM, Naime D, Vilček J, Cronstein BN, "TNF/IL-1-inducible protein TSG-6 potentiates plasmin inhibition by inter-α-inhibitor and exerts a strong anti-inflammatory effect in vivo," J Immunol, 1996, 156, 1609-1615.

Wisniewski HG, Maier R, Lotz M, Lee S, Klampfer L, Lee TH, et al, "TSG-6: A TNF-, IL-1-, and LPS-inducible secreted glycoprotein associated with arthritis," J Immunol, Dec. 1, 1993, 151(11), 6593-6601.

Wisniewski HG, Vilček J, "Cytokine-induced gene expression at the crossroads of innate immunity, inflammation and fertility: TSG-6 and PTX3/TSG-14," Cytokine Growth Factor Rev, 2004, 15(2-3), 129-146.

Yingsung W, Zhuo L, Mörgelin M, Yoneda M, Kida D, Watanabe H, et al, "Molecular heterogeneity of the SHAP-hyaluronan complex: Isolation and characterization of the complex in synovial fluid from patients with rheumatoid arthritis," J Biol Chem, Aug. 29, 2003, 278(35), 32710-32718.

Zhao M, Yoneda M, Ohashi Y, Kurono S, Iwata H, Ohnuki Y, et al, "Evidence for the covalent binding of SHAP, heavy chains of inter-α-trypsin inhibitor, to hyaluronan," J Biol Chem, Nov. 3, 1995, 270(44), 26657-26663.

Zhu L, Zhuo L, Kimata K, Yamaguchi E, Watanabe H, Aronica MA, et al, "Deficiency in the serum-derived hyaluronan-associated protein-hyaluronan complex enhances airway hyperresponsiveness in a murine model of asthma," Int Arch Allergy Immunol, 2010, 153, 223-233.

* cited by examiner

TREATMENT OF EXTRACELLULAR MATRIX TO REDUCE INFLAMMATION

CROSS-REFERENCE TO RELATED APPLICATIONS

This application is a continuation of U.S. application Ser. No. 13/489,974, filed Jun. 6, 2012, which claims the benefit of U.S. Provisional Application No. 61/520,173, filed Jun. 6, 2011, the entire disclosures of which are hereby incorporated herein by reference.

FIELD OF THE INVENTION

The present invention relates generally to treatment of extracellular matrix, and more particularly, to treatment of extracellular matrix to reduce inflammation.

BACKGROUND OF THE INVENTION

Inflammatory diseases, such as rheumatoid arthritis, affect millions of people worldwide. In the United States, rheumatoid arthritis affects more than 1% of the population, at a cost of approximately $15,000 to $20,000 per patient per year. Currently there is no cure for rheumatoid arthritis, which eventually leads to permanent joint damage and functional disability. Conventional treatments involve medications used to mediate the patient's immune system, globally affecting the immune response, to reduce or slow inflammation. For example, corticosteroids are used to reduce disease activity and joint inflammation acutely. However, their long-term use is inappropriate due to major side effects of chronic use including diabetes, cataracts, weight gain, and adrenal suppression. Corticosteroids are often used to control symptoms and flares of joint inflammation until disease-modifying anti-rheumatic drugs (also termed DMARDs) reach their full effectiveness, which can take up to 6 months.

Disease-modifying anti-rheumatic drugs can be divided into two general categories based on how they work: oral DMARDs and biological DMARDs. Oral DMARDs are taken by mouth. They interfere with the making or working of immune cells that cause joint inflammation. Biological DMARDs are given by injection (infusion). They act in several different ways to affect how immune cells work. DMARDs decrease joint inflammation and damage. Because they work throughout the body to fight rheumatoid arthritis, they are also associated with serious side effects, including life-threatening infections, hematologic issues, kidney and liver damage, severe immunosuppression and death, as well as long-term effects such as increased risk of cancer. Intense blood work is usually required to monitor the drug's effect. DMARDs are usually started within 3 months of diagnosis and are used to control the progression of rheumatoid arthritis and to try to prevent joint deterioration and disability.

Non-steroidal anti-inflammatory drugs (NSAIDs) such as aspirin, ibuprofen, or naproxen are used to control pain and may help reduce inflammation. They do not control the disease or stop it from progressing. NSAIDs may be combined with DMARDs.

None of the drug-based therapies currently in use are successful in halting the progression of inflammatory disease. Presently, the only option at end stage disease is total joint replacement. Accordingly, novel therapies for the treatment of inflammatory diseases, slowing or stopping their advance, and reducing the incidence and need for joint replacement surgeries, are desirable. Such therapies will preferably have a more localized action, and will not directly affect immune-system function or pathways, and thus produce unwanted side effects.

During inflammation, serum exudates enter tissues, bathing the macromolecular hyaluronan (also termed hyaluronate, hyaluronic acid, or HA) found in most tissue extracellular matrices (ECM) with the serum-derived proteoglycan inter-α-inhibitor (IαI). Heavy chains (HC) of IαI are transferred from IαI to HA by the enzyme tumor necrosis factor stimulated gene-6 (TSG-6), a protein expressed at sites of inflammation, causing a pathological transformation to the HA matrix. This pathological transformation functions as a specific ligand for inflammatory cells. The formation of HC-HA complexes transform normally benign HA matrix molecules into pathological HA that includes specific ligands for inflammatory cell receptors contributing to inflammatory disease processes through binding and activation of inflammatory cells. Strategies that would allow for the in vivo manipulation of HC transfer both to and from HA in inflamed tissues may provide a therapy for treatment of a wide variety of inflammatory diseases.

BRIEF SUMMARY OF THE INVENTION

In one example aspect, a pharmaceutical composition is provided. The composition comprises a compound comprising the hyaluronan-containing structure:

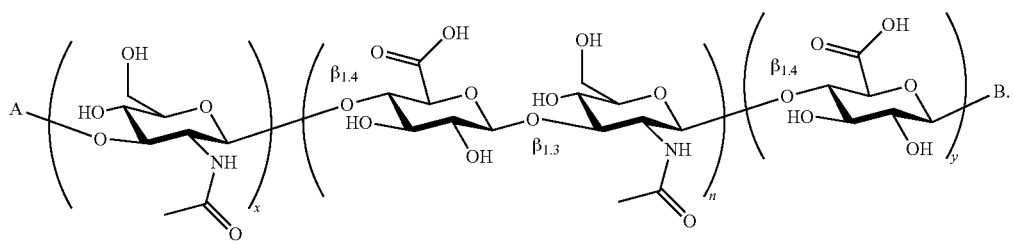

The composition also comprises a pharmaceutically acceptable excipient. In accordance with the composition, A is selected from the group consisting of hydrogen, a substituent that does not comprise a binding site for tumor necrosis factor stimulated gene-6 (TSG-6) protein, a substituent that interferes with binding of TSG-6 protein immediately adjacent thereto, and chondroitin. Also in accordance with the composition, B is selected from the group consisting of hydroxyl, a substituent that does not comprise a binding site for TSG-6 protein, a substituent that interferes with binding of TSG-6 protein immediately adjacent thereto, and chondroitin. Also in accordance with the composition, $x=0$ or 1, $y=0$ or 1, and $n=3$ to 70, with the proviso that if $n=3$, then at least one of x and $y=1$. The composition is suitable for administration by injection, inhalation, topical rub, or ingestion.

In another example aspect, a method of treating a site of inflammation in an individual in need thereof is provided. The method comprises administering to the site of the individual a therapeutically effective amount of a compound comprising the hyaluronan-containing structure:

[Chemical structure diagram]

In accordance with the method, A is selected from the group consisting of hydrogen, a substituent that does not comprise a binding site for TSG-6 protein, a substituent that interferes with binding of TSG-6 protein immediately adjacent thereto, and chondroitin. Also in accordance with the method, B is selected from the group consisting of hydroxyl, a substituent that does not comprise a binding site for TSG-6 protein, a substituent that interferes with binding of TSG-6 protein immediately adjacent thereto, and chondroitin. Also in accordance with the method, x=0 or 1, y=0 or 1, and n=3 to 70, with the proviso that if n=3, then at least one of x and y=1.

In another example aspect, a method of decreasing heavy chain modification of pathological hyaluronan at a site of inflammation in an individual in need thereof is provided. The method comprises administering to the site of the individual a therapeutically effective amount of a compound comprising the hyaluronan-containing structure:

[Chemical structure diagram]

In accordance with the method, A is selected from the group consisting of hydrogen, a substituent that does not comprise a binding site for TSG-6 protein, a substituent that interferes with binding of TSG-6 protein immediately adjacent thereto, and chondroitin. Also in accordance with the method, B is selected from the group consisting of hydroxyl, a substituent that does not comprise a binding site for TSG-6 protein, a substituent that interferes with binding of TSG-6 protein immediately adjacent thereto, and chondroitin. Also in accordance with the method, x=0 or 1, y=0 or 1, and n=3 to 70, with the proviso that if n=3, then at least one of x and y=1.

In another example aspect, a kit is provided. The kit comprises a compound comprising the hyaluronan-containing structure:

[Chemical structure diagram]

The kit also comprises a pharmaceutical excipient. The kit also comprises an instruction for use of the kit for treating a site of inflammation in an individual in need thereof by administering to the site a therapeutically effective amount of the compound. In accordance with the kit, A is selected from the group consisting of hydrogen, a substituent that does not comprise a binding site for TSG-6 protein, a substituent that interferes with binding of TSG-6 protein immediately adjacent thereto, and chondroitin. Also in accordance with the kit, B is selected from the group consisting of hydroxyl, a substituent that does not comprise a binding site for TSG-6 protein, a substituent that interferes with binding of TSG-6 protein immediately adjacent thereto, and chondroitin. Also in accordance with the kit, x=0 or 1, y=0 or 1, and n=3 to 70, with the proviso that if n=3, then at least one of x and y=1.

In another example aspect, a kit is provided. The kit comprises a compound comprising the hyaluronan-containing structure:

$$A-(glcNAc^*)_x-(glcA^*-glcNAc^*)_n-(glcA^*)_y-B$$

The kit also comprises a pharmaceutical excipient. The kit also comprises an instruction for use of the kit for decreasing heavy chain modification of pathological hyaluronan at a site of inflammation in an individual in need thereof by administering to the site a therapeutically effective amount of the compound. In accordance with the kit, A is selected from the group consisting of hydrogen, a substituent that does not comprise a binding site for TSG-6 protein, a substituent that interferes with binding of TSG-6 protein immediately adjacent thereto, and chondroitin. Also in accordance with the kit, B is selected from the group consisting of hydroxyl, a substituent that does not comprise a binding site for TSG-6 protein, a substituent that interferes with binding of TSG-6 protein immediately adjacent thereto, and chondroitin. Also in accordance with the kit, $x=0$ or 1, $y=0$ or 1, and $n=3$ to 70, with the proviso that if $n=3$, then at least one of x and $y=1$.

In another example aspect, a pharmaceutical composition is provided. The composition comprises a compound comprising the structure $A-(glcNAc^*)_x-(glcA^*-glcNAc^*)_n-(glcA^*)_y-B$. The composition also comprises a pharmaceutically acceptable excipient. In accordance with the composition, glcA* is D-glucuronic acid or substituted D-glucuronic acid, and glcNAc* is N-acetyl-D-glucosamine or substituted N-acetyl-D-glucosamine, with the proviso that $(glcNAc^*)_x-(glcA^*-glcNAc^*)_n-(glcA^*)_y$ includes at least one binding site for TSG-6 protein. Also in accordance with the composition, A is selected from the group consisting of hydrogen, a substituent that does not comprise a binding site for TSG-6 protein, a substituent that interferes with binding of TSG-6 protein immediately adjacent thereto, and chondroitin. Also in accordance with the composition, B is selected from the group consisting of hydroxyl, a substituent that does not comprise a binding site for TSG-6 protein, a substituent that interferes with binding of TSG-6 protein immediately adjacent thereto, and chondroitin. Also in accordance with the composition, $x=0$ or 1, $y=0$ or 1, and $n=3$ to 70, with the proviso that if $n=3$, then at least one of x and $y=1$. The composition is suitable for administration by injection, inhalation, topical rub, or ingestion.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF THE INVENTION

Figure 1:
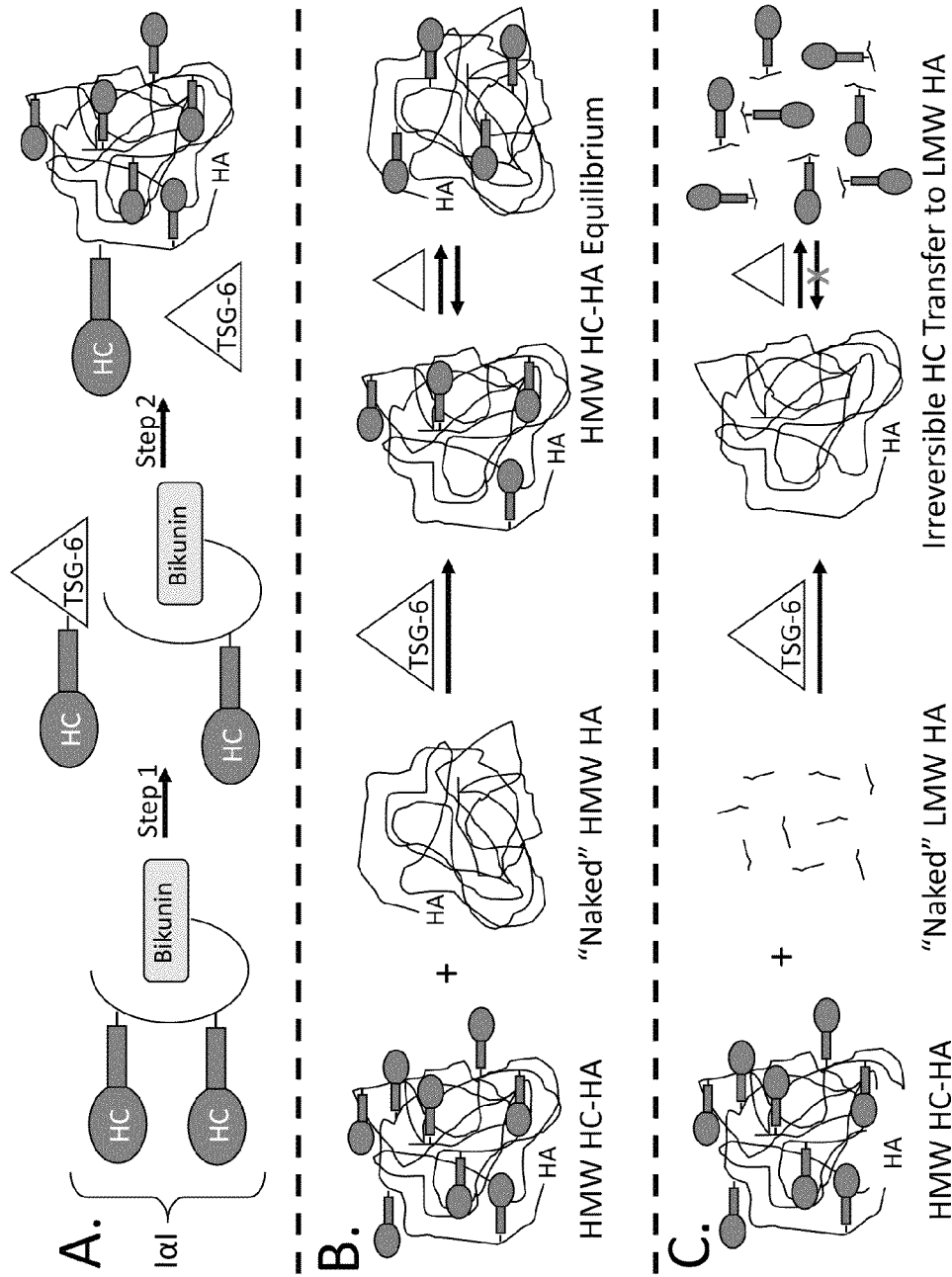
FIG. 1 is a schematic illustration of irreversible heavy chain transfer to LMW HA. (A) Inter-α-Inhibitor (IαI) has two HCs attached to the proteoglycan bikunin by covalent bonds with chondroitin sulfate (CS). TSG-6 removes a HC from IαI to form a HC-TSG-6 intermediate and transfers the HC onto the much larger HMW HA. (B) When "naked" HMW HA is mixed with HMW HC-HA, TSG-6 shuffles HCs between the two HA strands until the HCs are evenly distributed between the two strands. (C) When naked LMW HA is mixed with HMW HC-HA, TSG-6 transfers HCs onto LMW HA but it is unable to transfer them back to HMW HA.
Figure 2A:
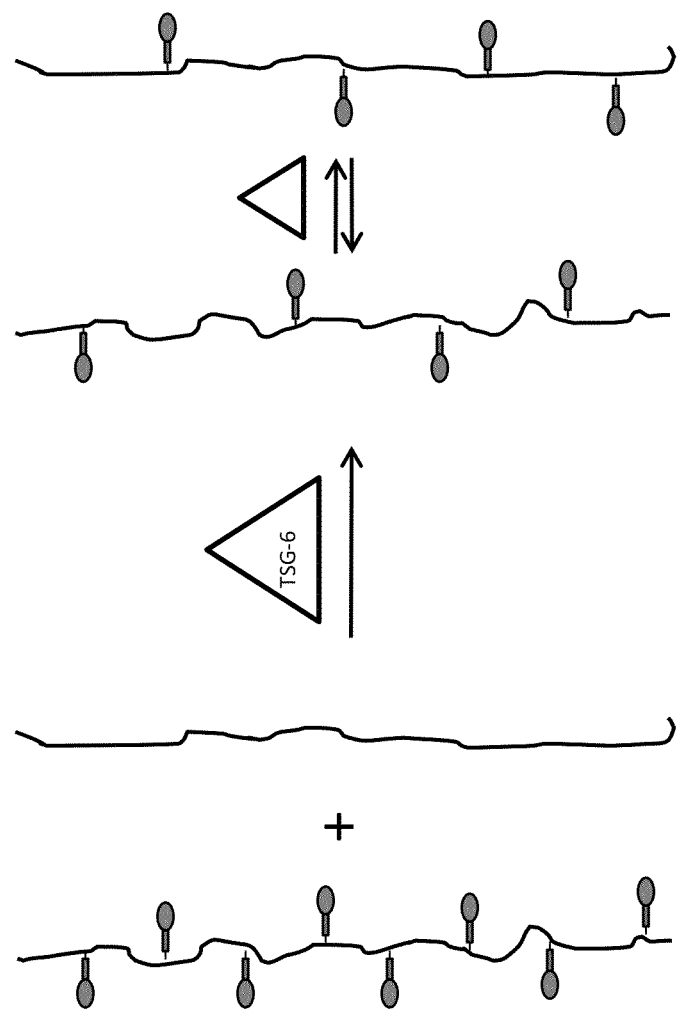
FIG. 2 is a schematic illustration of irreversible transfer of heavy chains (HC) from high molecular weight hyaluronan (HMW HA) to low molecular weight (LMW) HA via TSG-6. (A) HA is synthesized as a "naked" carbohydrate (i.e. lacking covalent binding partners) at the surface of cells. During inflammation, TSG-6 covalently transfers HC from serum-derived inter-α-inhibitor onto HA. HC covalently bound to HA can be shuttled between HMW HA chains by TSG-6 until they reach a reversible equilibrium. (B) LMW HA, such as HA that is 10 monosaccharides long (HA10) are also acceptors for HC transfer via TSG-6, but unlike HMW HC-HA, LMW HC-HA cannot serve as a donor for HC transfer. Thus, the transfers of HCs to LMW HA is irreversible.
Figure 2B:
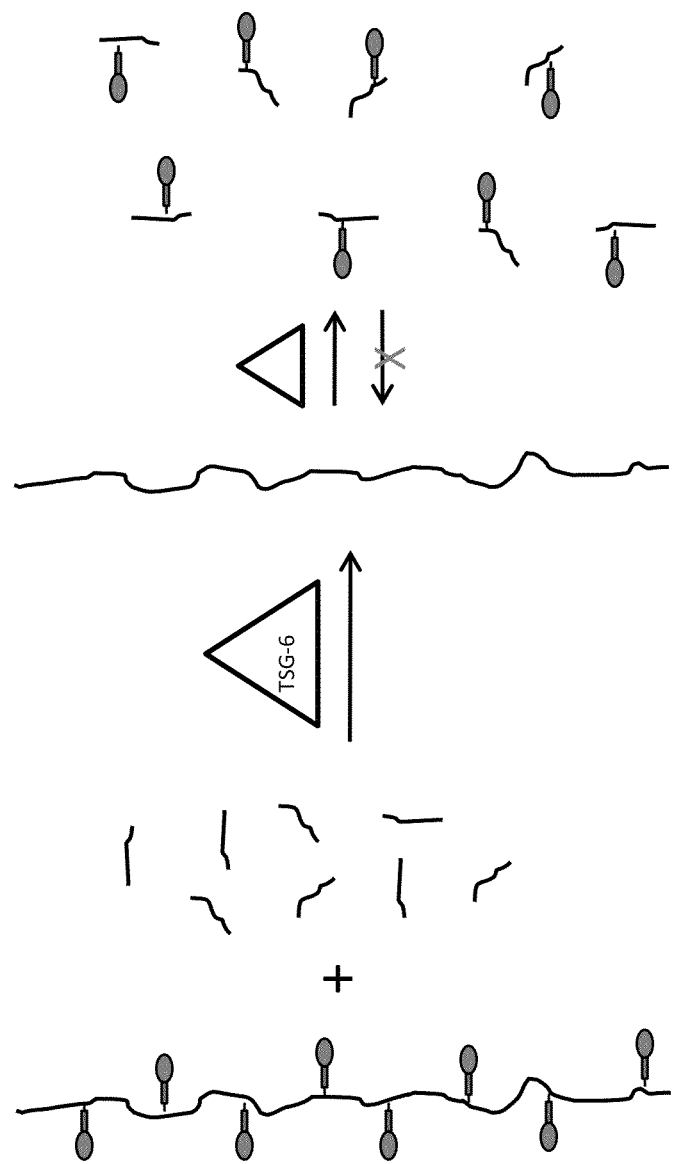

We have discovered that in the presence of TSG-6, HC can be irreversibly transferred from high molecular weight (HMW) HA to low molecular weight (LMW) HA thereby returning the pathological HA in the ECM to its original state (FIGS. 1 and 2). This is significant because pathological HA in the ECM of living tissues is HMW HA, which is typically in a molecular-weight range of, e.g., 1,000-5,000 kDa, but which can be greater than 10,000 kDa. For HMW HA, the TSG-6 mediated transfer of HC between HA molecules is a reversible process, resulting in the even distribution of HC along the lengths of all HMW HA chains present (FIGS. 1B and 2A). However, LMW HA (e.g. 8 to less than about 160 monosaccharides long) while also acceptors for HC transfer via TSG-6, cannot serve as donors for HC-transfer (FIGS. 1C and 2B). Irreversible swapping of HCs from HMW HA to LMW HA can potentially be exploited to remove HCs from pathological HC-HA matrices found in RA and other inflammatory diseases. The resulting LMW HA, modified with HC, is expected to be readily cleared from the joint space. This will remove HC from the joint matrix, and thus the leukocytes will not be retained. Moreover, HA molecules are neither known nor predicted to be toxic, antigenic, or allergenic. This provides a paradigm for quantitatively removing pathologic HC ligands from HA of inflamed tissues, potentially alleviating or eliminating inflammation, and providing patient relief by removing inflammatory-cell recruitment sites in the ECM of the affected joint or tissue. Administration of formulations of LMW HA in an affected joint or other tissue with exogenously supplied recombinant TSG-6 or endogenous TSG-6 would constitute a novel class of therapeutics for treatment of inflammatory conditions such as rheumatoid arthritis, psoriatic arthritis, psoriasis, inflammatory bowel disease, asthma, etc., and could potentially be used as a prophylactic to prevent initial onset of inflammatory disease.

Figure 3:
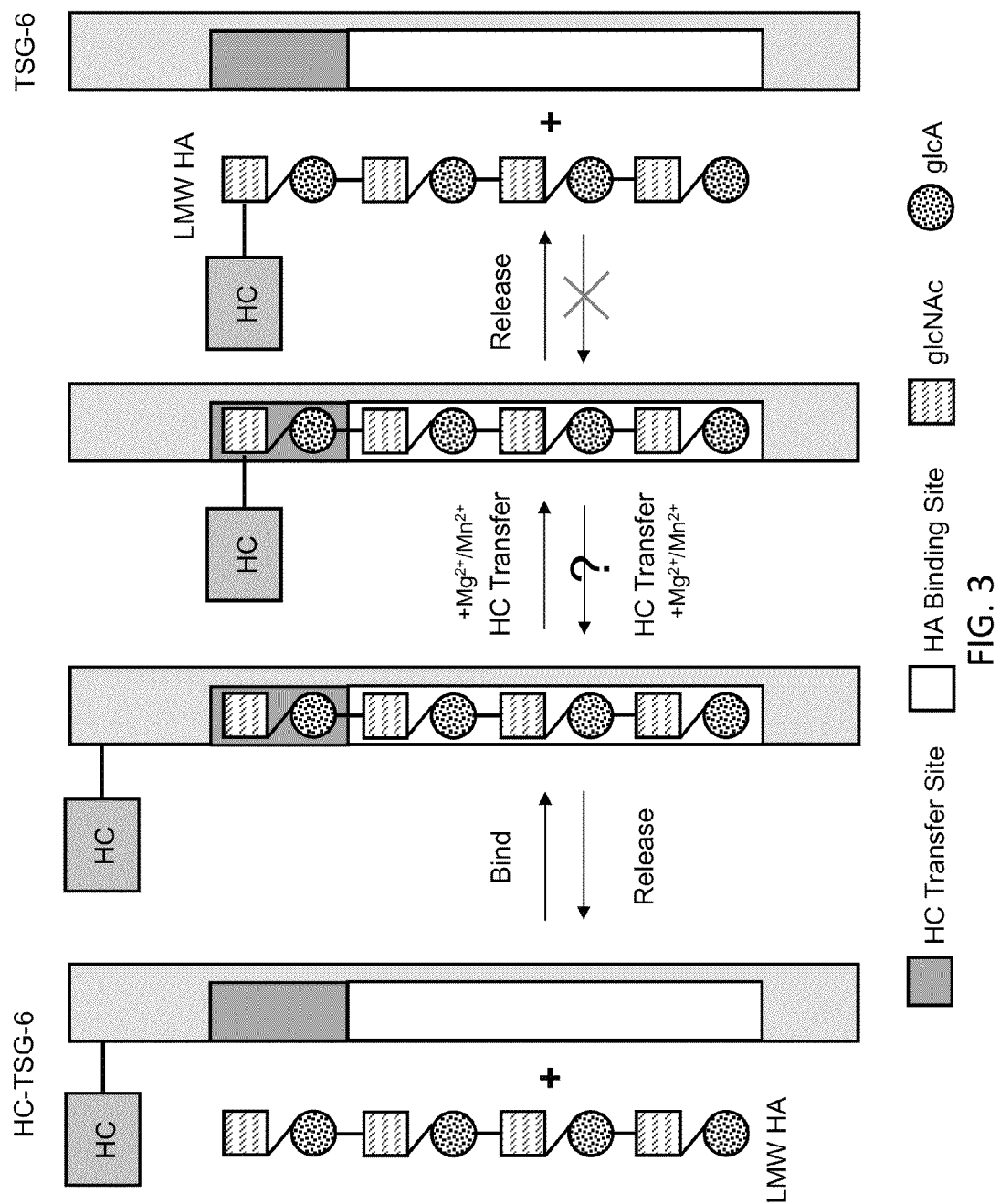
FIG. 3 shows schematically the irreversible effect of LMW HA (e.g. composed of 8 to less than about 160 monosaccharides) on TSG-6-catalyzed HC transfer to HA. LMW HA (e.g. HA composed of 8 monosaccharides as illustrated) is able to bind to TSG-6 and accept transfer of HC from TSG-6. However, once released from the TSG-6 enzyme, LMW HC-HA is itself unable to bind to TSG-6. Thus LMW HA can serve as a HC acceptor, but not HC donor.

For purposes of this disclosure, LMW HA refers to HA molecules having 8 to less than about 160 monosaccharide units, or a molecular weight in the range of about 1.5 kDa to less than about 30 kDa. We have shown particularly that LMW HA having 8 to 87 monosaccharides is effective in the disclosed methods. Without wishing to be bound by theory, it is believed that LMW HA is able to bind to TSG-6 and accept transfer of HC from TSG-6, but that once released from the TSG-6 enzyme, LMW HC-HA is itself unable to bind to TSG-6, and thus that LMW HA can serve as a HC acceptor, but not HC donor (FIG. 3).

Figure 4:
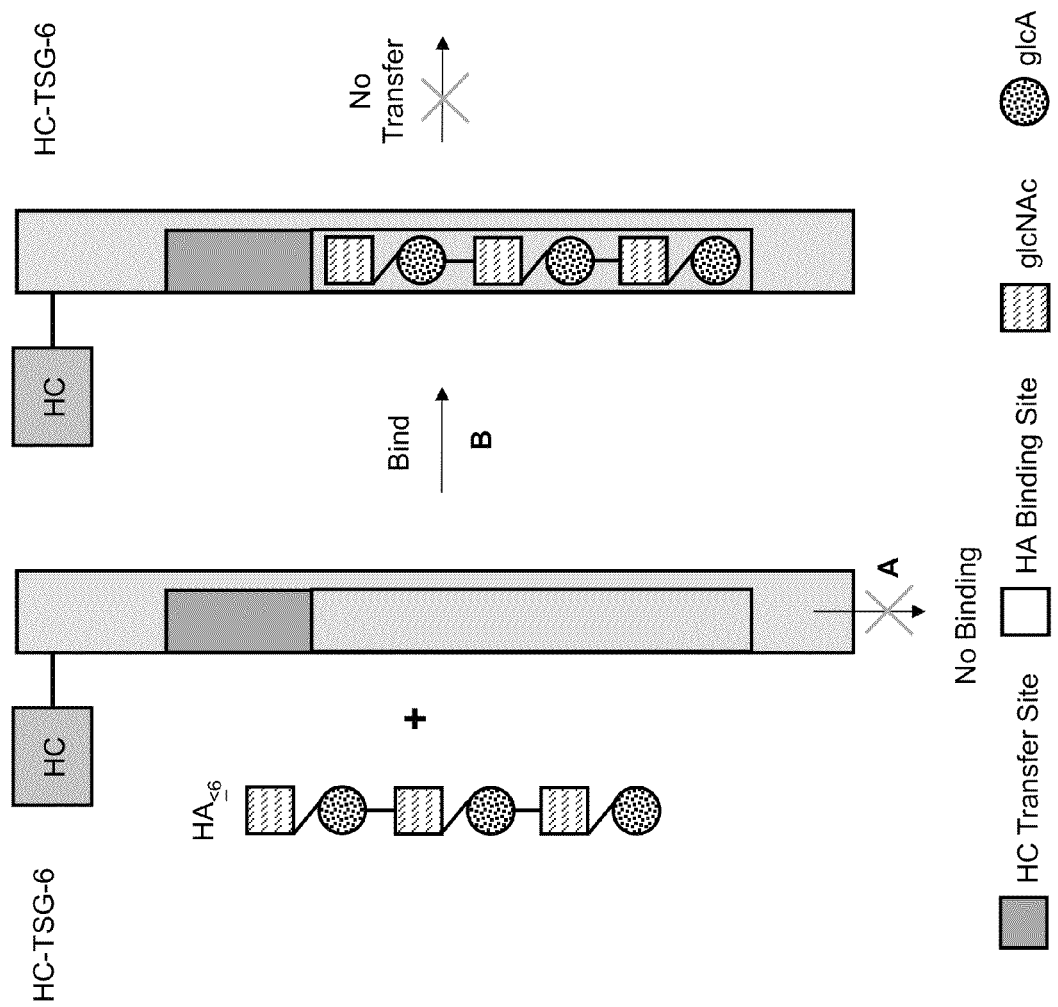
FIG. 4 shows schematically the lack of TSG-6 catalyzed HC transfer onto HA6 or less. HA composed of 6 or fewer monosaccharides does not accept HCs via a TSG-6-mediated reaction. This is believed to be because the small HA molecule is either: (A) too small to bind to the TSG-6 HA binding site; or (B) upon binding is too small to accept transfer of HC from TSG-6.

In contrast, HA molecules having 6 monosaccharides have been found to be unable to receive HCs via TSG-6-mediated transfer from tissue HA. Without wishing to be bound by theory, it is believed that HA molecules of 6 monosaccharides or smaller do not provide sufficient length for either binding to the TSG-6 enzyme, or if bound to the enzyme, for the enzyme to transfer a HC to the bound HA molecule (FIG. 4).

Of note, because HA is a molecule composed of repeat disaccharide units (D-glucuronic acid and N-acetyl-D-glucosamine linked via glycosidic bonds), it will not naturally occur in odd-numbered monosaccharide units. However, it may be possible to prepare a synthetic HA-analog having the same structure as HA but with only 7 monosaccharide units; i.e. excluding either a terminal D-glucuronic acid or N-acetyl-D-glucosamine residue. (It will be naturally recognized to persons of ordinary skill in the art that references to hyaluronan, hyaluronic acid, hyaluronate, or HA are understood to include conventional HA as well as such HA analogs having an odd number of monosaccharide units, for example due to the cleavage of a terminal monosaccharide from the HA chain). It is believed that a 7-monosaccharide HA analog may also serve as LMW HA in the disclosed methods.

Figure 5:
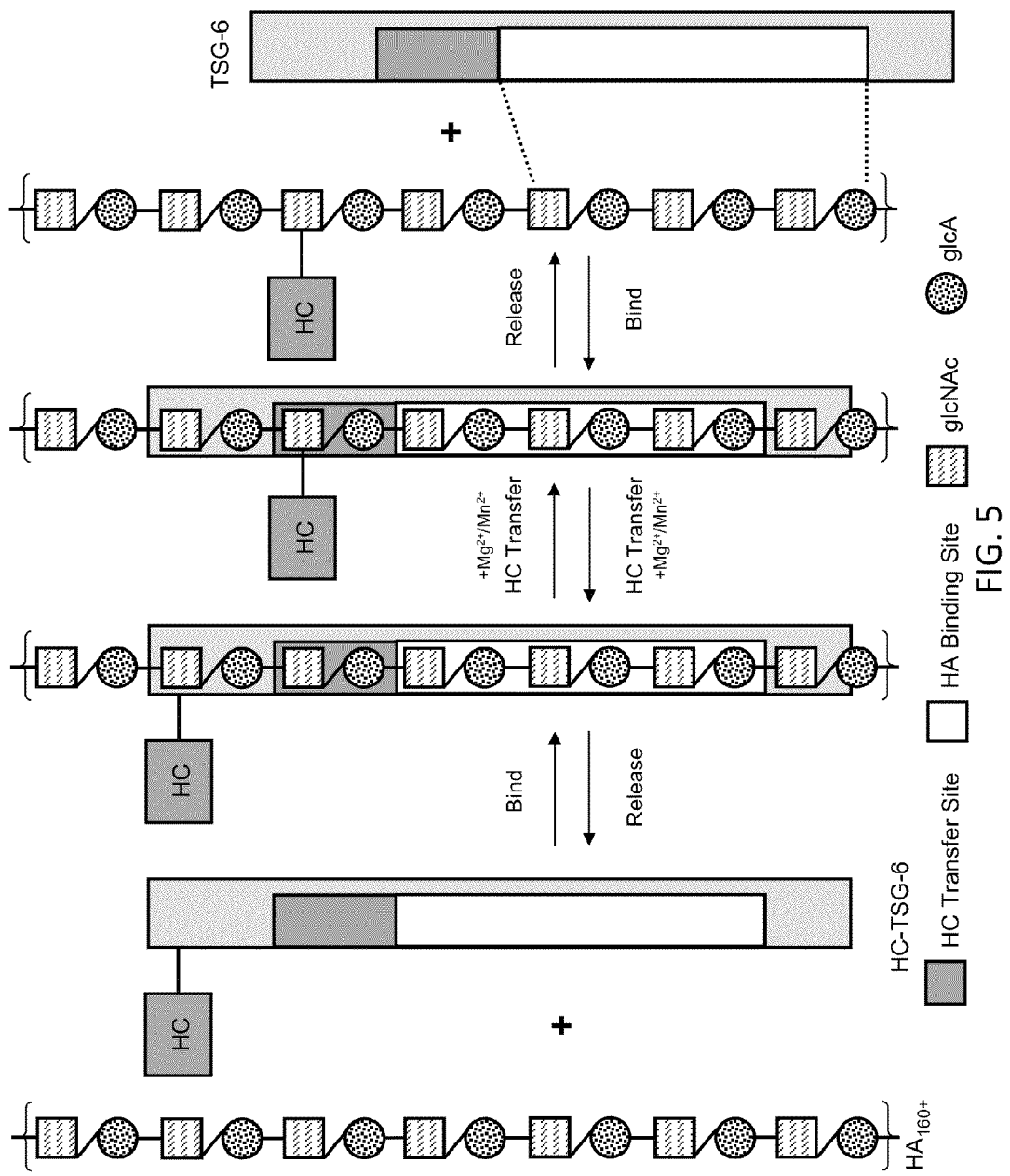
FIG. 5 shows schematically the reversible effect of HA160 or more (also termed HA160+) on TSG-6 catalyzed HC transfer to HA. HA composed of ~160 monosaccharides or more is able to bind to TSG-6 and accept transfer of HC from TSG-6. Once released from the TSG-6 enzyme the HC-HA160+ is able to bind to TSG-6 and transfer its HC back to TSG-6. The HA160+ without HC is then released by the enzyme. Thus HA composed of 160 monosaccharides or more can serve as both a HC acceptor and donor.

At the other end of the spectrum, we have determined that HA molecules having about 160 or more monosaccharides do not function like LMW HA in the disclosed methods because although they do accept HC transfer via a TSG-6-mediated reaction, they do so reversibly (FIG. 5).

Again without wishing to be bound by theory, it is believed that there is a range of HA lengths wherein the chain is long enough to initially bind TSG-6 so as to mediate the attachment of a HC, but not long enough for TSG-6 to bind again once the HC has been attached, so as to mediate the removal of the previously transferred HC. This range will constitute the range of permissible HA lengths (molecular weights) in the disclosed methods. As noted above, currently, the range of 8-87 monosaccharides is known to work as LMW HA molecules in the disclosed methods; that is, to irreversibly accept HCs transferred from tissue HA (which is HMW HA) via a TSG-6-mediated reaction. In preferred embodiments, the LMW HA will range from 8-25 monosaccharides in length, more preferably 8-20, 8-15 or 8-10 monosaccharides. However, LMW HA with monosaccharide lengths ranging up to 130 monosaccharide units (i.e. up to 25 kDa), and approaching less than about 160 monosaccharide units (i.e. less than about ~30 kDa), may be effective in the disclosed methods as LMW HA molecules.

For HA molecules in the range of 88 to less than about 160 monosaccharides, there may be a range where the molecules function as LMW HA in the disclosed methods depending on reaction kinetics and the precise location along the HA chain where the HC(s) is/are transferred. For example, based on the aforementioned TSG-6 transfer-site theory, if a HC is transferred to a 130 monosaccharide HA near a terminus, or if multiple HCs are transferred in close proximity to one another (e.g. within 6-8 monosaccharide units of length), there may be insufficient room for TSG-6 to re-bind to the HA adjacent the attached HC, resulting in a permanent transfer such that the HA molecule acts as LMW HA for the present methods. On the other hand, such chain lengths of 130 monosaccharides may provide sufficient binding space for TSG-6 adjacent a prior-attached HC moiety so that the attachment is reversible. In the latter instance, the HA molecule will not serve as LMW HA in the present methods. From the above, however, it will be appreciated that there will be a range of monosaccharide length (molecular weight) for HA molecules where they may transiently (i.e. under certain circumstances) behave as LMW HA so as to irreversibly accept HCs transferred from tissue HA according to the disclosed methods.

In practice, particularly in providing a therapy for treatment of inflammation, it will generally be desirable to select HA molecules whose length/molecular weight is sufficiently low so that it behaves consistently as LMW HA to irreversibly accept HCs as herein described. In addition to being easier to make and easier for the body to clear from an inflammatory site via natural processes, such LMW HA molecules will consistently irreversibly accept HCs, providing more efficient therapies based on known concentrations of LMW HA delivered. This is the reason that HA molecules of 8-25 monosaccharides in length are preferred. However, there may be instances where larger HA molecules having less than about 160 monosaccharides (i.e. <~30 kDa) could be used as the LMW HA in the disclosed methods. It is believed that HA molecules having about 160 monosaccharides or greater will consistently exhibit bulk reversible HC-transfer, making them unsuitable for use as LMW HA in the disclosed methods.

Based on the foregoing, the molecular weight of a LMW HA will be less than about 30 kDa. A HMW HA is one whose molecular weight is about 30 kDa or greater.

Figure 6A:
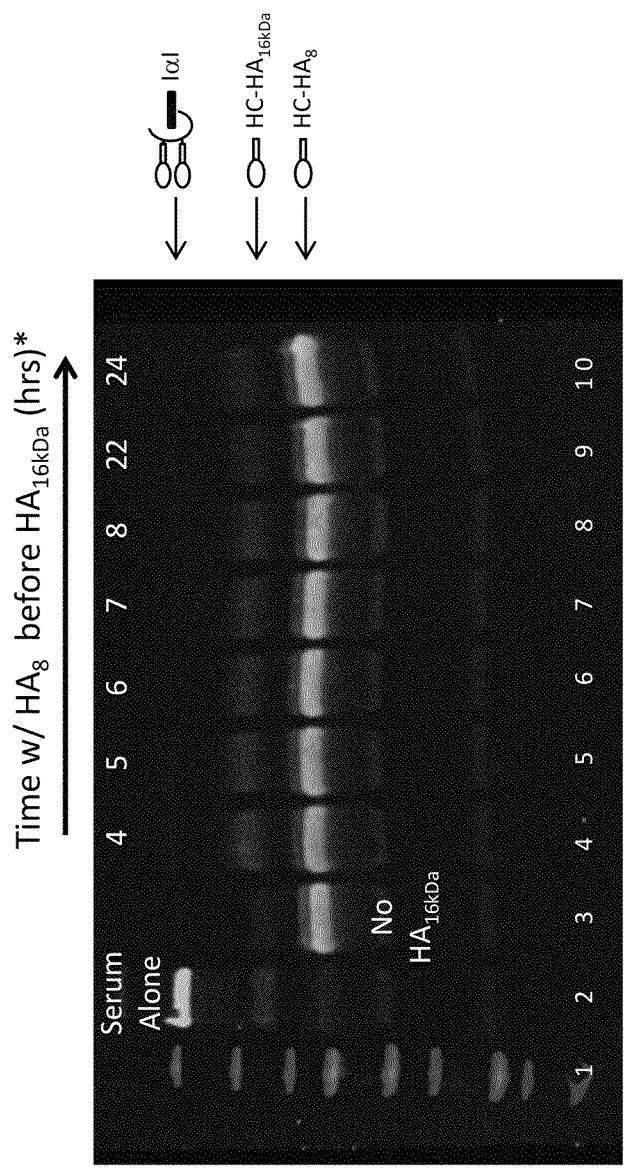
FIG. 6A-D shows results for kinetics of transfer of heavy chains (HCs), in which Western blots show the molecular weight gel shift of HCs transferred from inter-α-inhibitor (IαI) to hyaluronan (HA) and swapping between HA molecules of various sizes. Initial transfer of HC from IαI to (A) HA8, (B) HA16K, (C) HA50K, or (D) HA1000K, followed by introduction, at various time points, of (A) HA16K or (B-D) HA8.
Figure 6B:
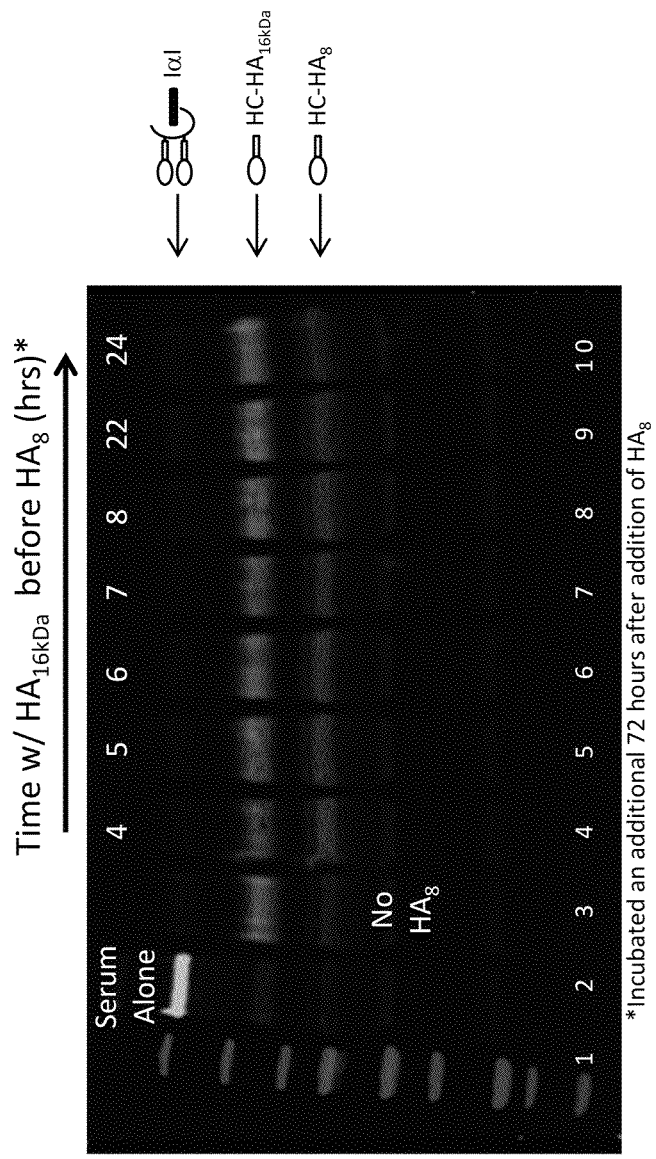
Figure 6C:
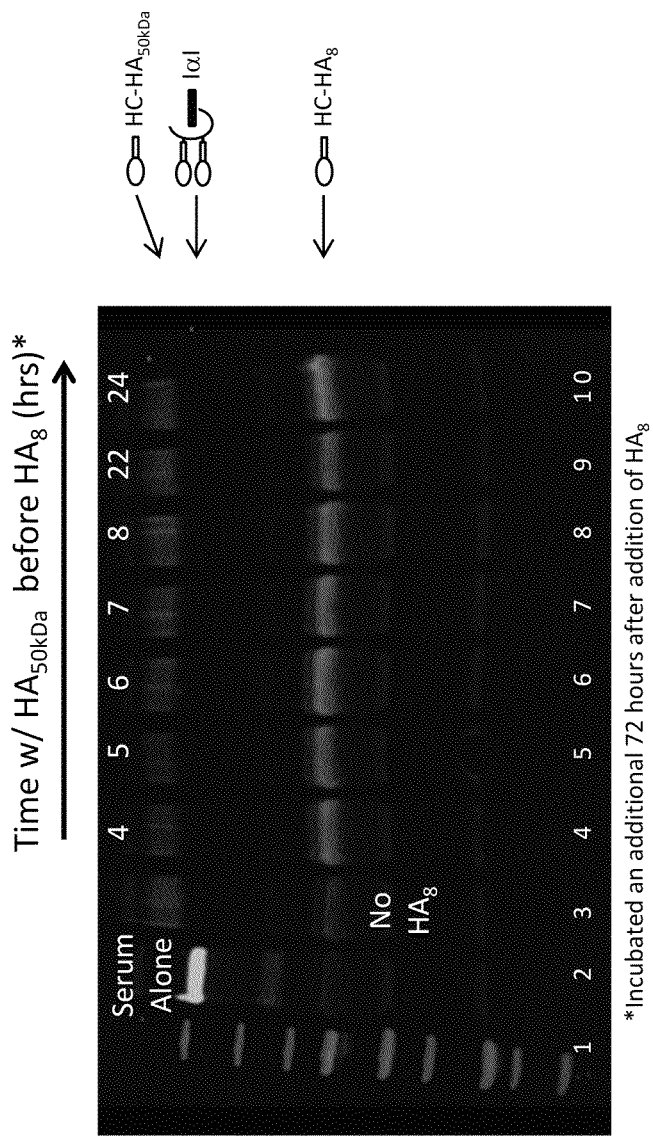
Figure 6D:
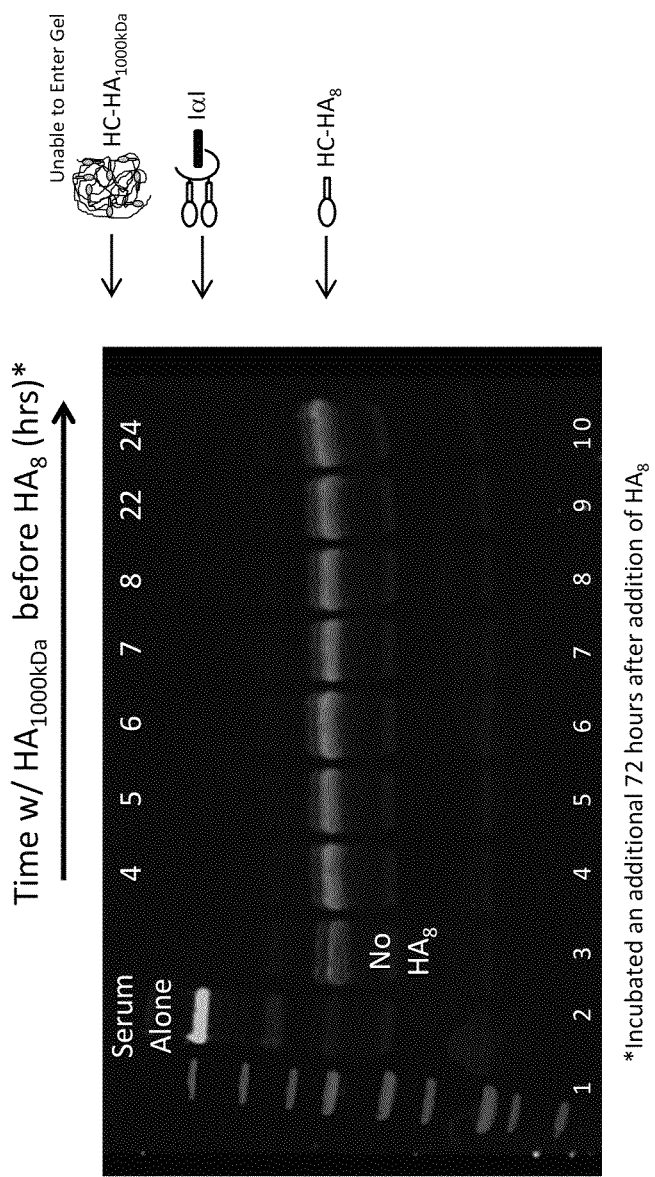

There is a kinetic component to the meaning of the term irreversible, as used herein. As can be seen in FIG. 6A, when HCs are transferred by TSG-6 from IαI to HA8 (HA that is 8 monosaccharides long) for different time periods before introducing HA16K (HA that is ~16 kDa in size), a small portion of HCs are transferred from the HC-HA8 to HA16K, which can be seen as a very faint band in lane 4, migrating where HC-HA16 kDa is marked on the right of the gel, that diminishes in intensity as time progresses. This suggests the presence of a small portion of HCs on HC-HA8 that are located on reversible sites within HA8. An alternative explanation is that HC transfer from IαI to HA8 was not complete at 4 hrs and that the HC-HA16 kDa band in lane 4, and thereafter, came from IαI and not HC-HA8. Regardless, the small proportion of HCs on HC-HA16 kDa decreases with incubation time, emphasizing the irreversible quality of HA8. As can be seen in FIG. 6B, when HCs are transferred by TSG-6 from IαI to HA16K for different times before introducing HA8, a small portion, but greater than that transferred from HA8 in FIG. 6A, of HCs are transferred from the HC-HA16K to the HA8 at the early time points, decreasing with time before addition of the HA8. Without wishing to be bound to theory, our interpretation is that because the HA16K is larger than the HA8, there is initially a greater proportion of reversible HCs on the HA16K than for the HA8, and it takes longer for these reversible HCs to be swapped by TSG-6 to irreversible sites on the HA16K. However, note that for both HA8 and HA16K, which are considered LMW HA domains capable of being HC acceptors but not donors, the majority of HC transfer from IαI is initially irreversible, with the degree of irreversibility increasing with time. As can be seen in FIG. 6C, when HCs are transferred by TSG-6 from IαI to HA50K (HA that has a molecular weight of 30.6 kDa as determined by multi-angle laser light scattering size exclusion chromatography, also termed MALLS-SEC) for different times before introducing HA8, the majority of the HCs are transferable to the HA8 as HA50K is considered HMW HA that is both a HC acceptor and donor. A similar result is seen in FIG. 6D for HA1000K (HA that is ~1000 kDa in size). Note, for HA50K and HA1000K, while they are considered HMW HA, and thus not irreversible HC acceptors, but rather HC acceptors and donors as used herein, not all of the HCs have been swapped from HA50K and HA1000K to HA8 when the HCs were first transferred to HA50K and HA1000K for 24 hours before the addition of HA8, suggesting that even HMW HAs such as HA50K and HA1000K may contain small amounts of HCs attached irreversibly. Alternatively, a longer incubation period than 72 hrs may be required to remove all of the HCs from HC-HA50K and HC-HA1000K. Thus there is a temporal and size component to irreversibility as used herein.

Considering example aspects of the compositions, methods, and kits disclosed herein in more detail, in one example aspect a pharmaceutical composition is provided. The composition comprises a compound comprising the hyaluronan-containing structure:

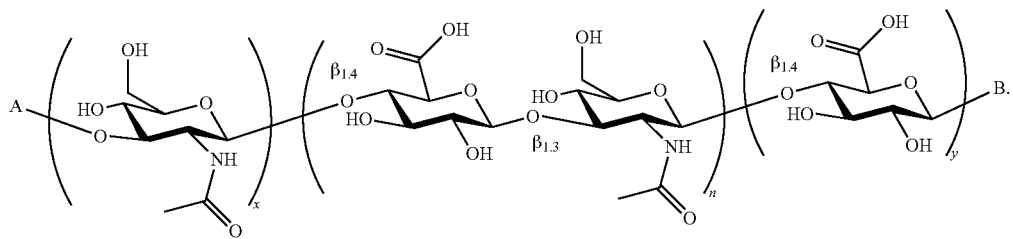

In accordance with the composition, A is selected from the group consisting of hydrogen (i.e. H), a substituent that does not comprise a binding site for TSG-6 protein, a substituent that interferes with binding of TSG-6 protein immediately adjacent thereto, and chondroitin.

The substituent that does not comprise a binding site for TSG-6 protein can be, for example, a monosaccharide, oligosaccharide, polysaccharide, alkyl group, or functional group, or a modified or derivatized version thereof, that is not recognized as a binding site by TSG-6 protein and thus to which TSG-6 protein cannot bind. Based on the disclosure herein, one of ordinary skill would be able to identify and confirm any of a wide range of substituents for use in this regard without undue experimentation or effort.

The substituent that interferes with binding of TSG-6 protein immediately adjacent thereto can be, for example, a bulky adduct, a monosaccharide substituted with a bulky adduct, or a polysaccharide substituted with a bulky adduct, the bulky adduct being positioned immediately adjacent the remainder of the structure. The bulky adduct can be, for example, a tyramine group or a hydroxyphenyl group. The monosaccharide substituted with a bulky adduct can be, for example, a D-glucuronic acid residue, substituted with a tyramine group or a hydroxyphenyl group. The polysaccharide substituted with a bulky adduct can be, for example, HMW hyaluronan substituted by one or more tyramine or hydroxyphenyl groups, at least one of the tyramine or hydroxyphenyl groups being positioned immediately adjacent the remainder of the structure.

By the substituent interfering with binding of TSG-6 protein, it is meant that the substituent prevents TSG-6 protein from binding the part of the structure immediately adjacent to the substituent, at least to the extent of preventing TSG-6 from removing an IαI heavy chain that has been attached to that part of the structure.

Chondroitin is a glycosaminoglycan that includes a disaccharide repeat of N-acetylgalactosamine and glucuronic acid. The disaccharide of chondroitin is thus identical to that of HA except for the conformation of one hydroxyl group. Chondroitin can be bound by TSG-6, with subsequent heavy chain transfer, though less effectively than for HA.

Also in accordance with the composition, B is selected from the group consisting of hydroxyl (i.e. OH), a substituent that does not comprise a binding site for TSG-6 protein, a substituent that interferes with binding of TSG-6 protein immediately adjacent thereto, and chondroitin. As one of ordinary skill will recognize from the structure as drawn, in contrast to A, which is linked to the remainder of the structure via the non-reducing end of a saccharide, B is linked to the remainder of the structure via the reducing end of a saccharide. Taking this difference into account, the substituent that does not comprise a binding site for TSG-6 protein and the substituent that interferes with binding of TSG-6 protein immediately adjacent thereto for B otherwise can be, for example, as described above for A.

Also in accordance with the composition, $x=0$ or 1, $y=0$ or 1, and $n=3$ to 70, with the proviso that if $n=3$, then at least one of x and $y=1$.

As one of ordinary skill will appreciate from the foregoing, the hyaluronan-containing structure comprises a LMW HA domain between A and B. Specifically, this structure comprises the disaccharide repeating unit of hyaluronan, i.e. a disaccharide with alternating β (1-3) glucuronidic acid and β (1-4) glucosaminidic bonds, in this case with a degree of polymerization of 3 to 70. The disaccharide is flanked, at its nonreducing end, by A and optionally an N-acetyl-D-glucosamine residue therebetween. The disaccharide is also flanked, at its reducing end, by B and optionally a D-glucuronic acid residue therebetween. As will be appreciated, if the degree of polymerization of the disaccharide repeating unit is 3, then at least one of the flanking N-acetyl-D-glucosamine residue or D-glucuronic acid residue must be present. Accordingly, the structure includes at least seven consecutive monosaccharides of hyaluronan between A and B. As will also be appreciated, if the structure is not terminated by hydrogen at its nonreducing end, it will be terminated there by the substituent that does not comprise a binding site for TSG-6 protein, the substituent that interferes with binding of TSG-6 protein immediately adjacent thereto, or chondroitin. Likewise, if the structure is not terminated by hydroxyl at its reducing end, it will be terminated there by the substituent that does not comprise a binding site for TSG-6 protein, the substituent that interferes with binding of TSG-6 protein immediately adjacent thereto, or chondroitin. Accordingly, the structure does not include more than 142 consecutive monosaccharides of hyaluronan between A and B, nor can the part of the structure between A and B be recognized by TSG-6 as if the part were HMW HA.

The composition also comprises a pharmaceutically acceptable excipient. A pharmaceutically acceptable excipient refers to an excipient that causes no significant adverse toxicological effects to the patient. Suitable pharmaceutical excipients include, for example, water for injection, carbohydrates, inorganic salts, antimicrobial agents, antioxidants, surfactants, buffers, acids, bases, divalent cations (e.g. $Mg^{+2}$ or $Mn^{+2}$), and combinations thereof.

The composition is suitable for administration by injection, inhalation, topical rub, or ingestion. As used herein, suitable for administration by injection, inhalation, topical rub, or ingestion means that the composition would be considered acceptable for therapeutic application, e.g. for a human, a dog, a cat, or a horse, by injection, inhalation, topical rub, or ingestion. In this regard, the pharmaceutical composition typically would need to be sterile, substantially pyrogen-free, and have no medically unacceptable effects. For example, the composition should not produce a medically unacceptable immunological reaction when injected into a human subject. Medically unacceptable effects can be determined by one of ordinary skill in the field of medicine. The composition can be made suitable for administration by injection, inhalation, topical rub, or ingestion by routine methods that are known in the art, such as purification of the compound, the pharmaceutically acceptable excipient, and other components prior to addition to the composition, and formulating, storing, and testing the composition by standard methods, and thus can be obtained without undue experimentation or effort.

Considering the compound in more detail, the compound can be one produced by a non-biological process. For example, as discussed in detail below, LMW HA can be made enzymatically by published and patented processes, based on extension of short HA chains (or primers) into much longer HA chains by recombinant *Escherichia coli*-derived HA synthase of *Pasteurella multocida* (PmHAS). These approaches offer benefits such as precise control over the degree of polymerization of the LMW HA molecules and higher purity of final product in comparison to biological processes for production and purification of HA.

The compound can be, for example, one in which A is hydrogen and B is hydroxyl, thus corresponding to a LMW HA without any non-saccharide substituents.

Also for example, the compound can be one in which A is the substituent that does not comprise a binding site for TSG-6 protein, A being a saccharide, and B is the substituent that does not comprise a binding site for TSG-6 protein, B being a saccharide. Such a compound may include as A and B, for example, saccharides other than those that naturally occur in HA and that do not otherwise include a binding site for TSG-6 protein.

Also for example, the compound can be one in which A is the substituent that interferes with binding of TSG-6 protein immediately adjacent thereto, A being hyaluronan modified with tyramine, and B is the substituent that interferes with binding of TSG-6 protein immediately adjacent thereto, B being hyaluronan modified with tyramine. For example, the compound can be hyaluronan with a tyramine substitution of about 1 tyramine adduct about every 20 to 90 monosaccharides, or about every 30 to 50 monosaccharides, or about every 40 monosaccharides. As one of ordinary skill will appreciate based on the disclosure herein, TSG-6 protein will interact with such hyaluronan modified with tyramine by adding HC chains irreversibly, as though the parts of the hyaluronan molecules between the tyramine substitutions were LMW HA, i.e. attachment of HC to these parts by TSG-6 will be irreversible.

Also for example, the compound can be, for example, one in which A is chondroitin and B is chondroitin, thus corresponding to a chimera of chondroitin-LMW HA-chondroitin. In such a chimera, the chondroitin may serve the purpose of interrupting, or setting off, the LMW HA, ensuring that it is recognized as a LMW HA domain by TSG-6.

The composition can be one wherein, e.g. n=3 to 65 (corresponding to approximately 7 to 132 monosaccharide units), n=3 to 45 (corresponding to approximately 7 to 92 monosaccharide units), or n=3 to 12 (corresponding to approximately 7 to 26 monosaccharide units). The composition can also be one wherein n=41 to 45 (corresponding to approximately 82 to 92 monosaccharide units), or n=43 to 44 (corresponding to approximately 86 to 90 monosaccharide units).

The composition can be, for example, one wherein A is hydrogen; B is hydroxyl; x, n, and y are selected from the group consisting of: (i) x=0, n=4, and y=0; (ii) x=0, n=5, and y=0, (iii) x=0, n=6, and y=0; (iv) x=0, n=7, and y=0; (v) x=0, n=9, and y=0; (vi) x=1, n=10, and y=0; and (vii) x=0, n=10, and y=1. The composition can also be, for example, one wherein A is hydrogen; B is hydroxyl; x, n, and y are selected from the group consisting of: (i) x=0, n=43, and y=0; (ii) x=1, n=43, and y=0, (iii) x=0, n=43, and y=1; (iv) x=1, n=43, and y=1; and (v) x=0, n=44, and y=0.

The composition can include the compound in a particular range of molecular weights, i.e. the composition can include more than one structural embodiment of the compound. For example, the composition can have a low polydispersity index, e.g. a polydispersity index of less than 1.10, less 1.05, or less than 1.02, with respect to the compound. Polydispersity index, as used herein, means the ratio of weight average to number average molecular weights. The composition can also be monodisperse (i.e. have a polydispersity index of 1.00) with respect to the compound. As will be appreciated from the disclosure herein, preparation of the composition such that the compound is present predominantly or entirely in one or a few particular molecular weight ranges may provide advantages in terms of control of residence times of the compound in tissues (more rapid clearance of lower molecular weight compounds) and viscosity of the composition (lower viscosity for lower molecular weight compounds).

The composition can further comprise a protein that transfers heavy chains of serum-derived proteoglycan bikunin to the compound. As one of ordinary skill will appreciate from this disclosure, co-administration of the compound and such a protein to a site of inflammation may provide for more rapid and effective transfer of HC to the compound during therapeutic use, by supplementing the corresponding endogenous protein at the site. The protein that transfers heavy chains of serum-derived proteoglycan bikunin to the compound can be, for example, a mammalian TSG-6 protein, a human TSG-6 protein, a canine TSG-6 protein, a feline TSG-6 protein, and an equine TSG-6 protein. Such a protein may be obtained, for example, by purification from a natural source. Such a protein may also be obtained, for example, in a recombinant form, e.g. based on expression and purification from a recombinant host or system. Such a protein may also be obtained, for example, by genetic engineering, e.g. by mutating or otherwise modifying a naturally occurring form of TSG-6 to form a novel version of TSG-6 that nonetheless retains the enzymatic properties of TSG-6 protein. Methods for obtaining and/or modifying proteins as described above are well known in the art.

In another example aspect, a method of treating a site of inflammation in an individual in need thereof is provided. The method comprises administering to the site of the individual a therapeutically effective amount of a compound comprising the hyaluronan-containing structure:

the structure being as described above. Thus, for example, the method can comprise administering any of the compounds comprising the structure as described above.

In accordance with this method, the administering can comprise, for example, administering a composition comprising the compound and a pharmaceutically acceptable excipient by injection, inhalation, topical rub, or ingestion. Thus, for example, the administering can comprise administering any of the compositions comprising the compound and the pharmaceutically acceptable excipient as described above. The administering can be carried out once or multiple times, as needed, in order to treat the inflammation.

The method can also further comprise administering, at the site, a protein that transfers heavy chains of serum-derived proteoglycan bikunin to the compound, e.g. mammalian TSG-6 protein, recombinant mammalian TSG-6 protein, human TSG-6 protein, or recombinant human TSG-6 protein, e.g. in a naturally occurring or recombinant form.

In accordance with this method, the therapeutically effective amount of the compound can be, for example, 0.3 to 8 mass equivalents of pathological hyaluronan at the site, or 0.5 to 5 mass equivalents, 0.7 to 3 mass equivalents, 0.8 to 2 mass equivalents, 0.9 to 1.5 mass equivalents, or about 1 mass equivalent. The therapeutically effective amount of the compound can also be, for example, 2 to 7 mass equivalents of pathological hyaluronan at the site, or 3 to 6 mass equivalents, 4 to 5 mass equivalents, or about 4.5 mass equivalents.

The individual to be treated can be, for example, a mammal, such as a human, a dog, a cat, or a horse.

The inflammation at the site to be treated can be inflammation caused by an inflammatory condition such as, for example, rheumatoid arthritis, psoriatic arthritis, psoriasis, inflammatory bowel disease, or asthma.

In another example aspect, a method of decreasing heavy chain modification of pathological hyaluronan at a site of inflammation in an individual in need thereof is provided. The method comprises administering to the site of the individual a therapeutically effective amount of a compound comprising the hyaluronan-containing structure:

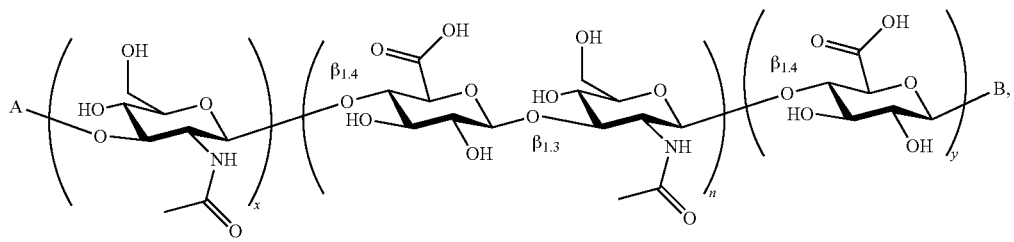

the structure being as described above. As will be appreciated, this method can also be carried out as described above, for example based on administering any of the compounds comprising the structure as described above, e.g. by injection, inhalation, topical rub, or ingestion, e.g. by administering any of the compositions comprising the compound and the pharmaceutically acceptable excipient as described above.

In another example aspect, a kit is provided. The kit comprises a compound comprising the hyaluronan-containing structure:

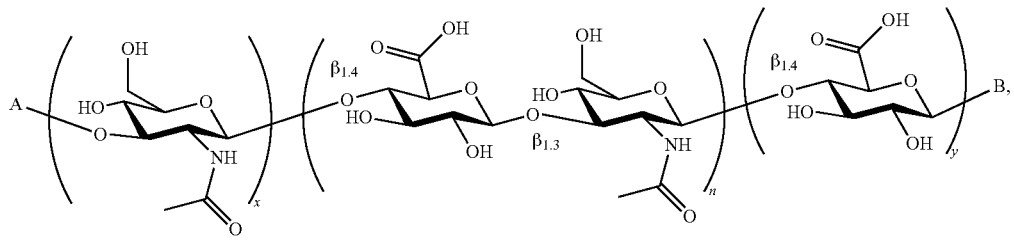

the structure being as described above. Thus, for example, the kit can comprise any of the compounds comprising the structure as described above. The kit also comprises a pharmaceutical excipient, the pharmaceutical excipient also being as described above. Thus, for example, the kit can comprise any of the compositions comprising the compound and the pharmaceutically acceptable excipient as described above. The kit also comprises an instruction for use of the kit for treating a site of inflammation in an individual in need thereof by administering to the site a therapeutically effective amount of the compound.

The kit can further comprise a protein that transfers heavy chains of serum-derived proteoglycan bikunin to the compound, again e.g. mammalian TSG-6 protein, recombinant mammalian TSG-6 protein, human TSG-6 protein, or recombinant human TSG-6 protein, e.g. in a naturally occurring or recombinant form. The individual can be, for example, a mammal, again e.g. a human, a dog, a cat, or a horse. The inflammation at the site can be caused, for example, by an inflammatory condition, again e.g. rheumatoid arthritis, psoriatic arthritis, psoriasis, inflammatory bowel disease, or asthma.

In another example aspect, a kit is provided. The kit comprises a compound comprising the hyaluronan-containing structure:

$$A-(glcNAc^*)_x-(glcA^*-glcNAc^*)_n-(glcA^*)_y-B$$

the structure being as described above, and thus can comprise any of the compounds comprising the structure as described above. The kit also comprises a pharmaceutical excipient, the pharmaceutical excipient also being as described above, and thus can comprise any of the compositions comprising the compound and the pharmaceutically acceptable excipient as described above. The kit also comprises an instruction for use of the kit for decreasing heavy chain modification of pathological hyaluronan at a site of inflammation in an individual in need thereof by administering to the site a therapeutically effective amount of the compound. As will be appreciated, the kit can also be configured as described above, e.g. to comprise a protein that transfers heavy chains of serum-derived proteoglycan bikunin to the compound. The kit also can be used for treatment of an individual being a mammal, e.g. a human, a dog, a cat, or a horse. The kit also can be used for treatment of an inflammatory condition such as rheumatoid arthritis, psoriatic arthritis, psoriasis, inflammatory bowel disease, or asthma.

In another example aspect, a pharmaceutical composition is provided. The composition comprises a compound comprising the structure $A-(glcNAc^*)_x-(glcA^*-glcNAc^*)_n-(glcA^*)_y-B$. The composition also comprises a pharmaceutically acceptable excipient. In accordance with the composition, glcA* is D-glucuronic acid or substituted D-glucuronic acid, and glcNAc* is N-acetyl-D-glucosamine or substituted N-acetyl-D-glucosamine, with the proviso that $(glcNAc^*)_x-(glcA^*-glcNAc^*)_n-(glcA^*)_y$ includes at least one binding site for TSG-6 protein. Also in accordance with the composition, A is selected from the group consisting of hydrogen, a substituent that does not comprise a binding site for TSG-6 protein, a substituent that interferes with binding of TSG-6 protein immediately adjacent thereto, and chondroitin. Also in accordance with the composition, B is selected from the group consisting of hydroxyl, a substituent that does not comprise a binding site for TSG-6 protein, a substituent that interferes with binding of TSG-6 protein immediately adjacent thereto, and chondroitin. Also in accordance with the composition, x=0 or 1, y=0 or 1, and n=3 to 70, with the proviso that if n=3, then at least one of x and y=1. The composition is suitable for administration by injection, inhalation, topical rub, or ingestion.

As one of ordinary skill will appreciate, like the compound comprising the hyaluronan-containing structure:

the compound comprising the structure $A-(glcNAc^*)_x-(glcA^*-glcNAc^*)_n-(glcA^*)_y-B$ can also be used in the methods and kits disclosed herein, based on irreversible transfer of HC thereto. Based on the disclosure herein, one of ordinary skill would be able to identify and confirm any of a wide range of compounds comprising the structure $A-(glcNAc^*)_x-(glcA^*-glcNAc^*)_n-(glcA^*)_y-B$ for use in such methods and kits without undue experimentation or effort.

In another example aspect, controlled and extended release of the LMW HA oligosaccharides in tissues subject to or experiencing inflammation may be achieved through encapsulation in tyramine-based (TB) HA hydrogels. Such gels are described in detail in U.S. Pat. Nos. 6,982,298, 7,368,502, 7,465,766, 8,021,350, 8,080,260, 8,137,688, and 8,138,265, the contents of which are incorporated herein by reference. LMW HA encapsulated in TB-HA hydrogels would be released at a rate predicted based on the size of the LMW HA and the porosity (concentration) of the HA in the TB-HA hydrogel, making the LMW HA accessible to TSG-6 enzyme for quantitative transfer of HC thereto. Such gels, implanted at an inflammation site, may also be broken down over time via the natural action of native hyaluronidase or free radicals, thus further releasing encapsulated LMW HA, making the latter accessible to TSG-6 enzyme for quantitative transfer of HC thereto. Alternatively, an implanted HA hydrogel itself may serve as a supply for LMW HA, whereby hyaluronidase or free radical mediated cleavage of HA chains in the gel releases smaller HA chains of appropriately low molecular weight, such that the released LMW HA chains are effective to irreversibly transfer HC attached thereto via the action of TSG-6 in vivo.

In another example aspect, a periodically-substituted HMW HA can be used to supply LMW-HA domains that will function as LMW HA in the disclosed methods. For example, tyramine-substituted HMW HA molecules (e.g., the same or similar molecules used to prepare the aforementioned TB-HA hydrogels in the above-incorporated patents) have tyramine adducts substituted onto the HA backbone at spaced or periodic locations along the macromolecular HA length. For example, to prepare the TB-HA hydrogels mentioned above HMW HA molecules having a periodicity of tyramine substitution of about 1 tyramine adduct every ~40 monosaccharides is preferred. The periodic spacing of tyramine adducts presents a series of discrete LMW-HA domains along the length of the HMW HA macromolecule, wherein each of the LMW-HA domains is accessible to TSG-6 enzyme for quantitative transfer of HC thereto. Thus, according to this embodiment a HMW HA macromolecule can be prepared that provides a series of LMW-HA domains separated by period adduct species where the adduct will not be recognized by the TSG-6 enzyme as native HA, and which will accordingly prevent or inhibit binding of that enzyme to mediate HC transfer from the LMW-HA domain. These domains thus will act like LMW HA if the non-native adducts (e.g. tyramine) are substituted on the HMW HA backbone with an appropriate periodicity to generate LMW-HA domains that serve as irreversible acceptors for HC transfer. As will be appreciated, the tyramine-substitution rate can be selected to provide the desired level of periodicity to correspond to the desired LMW-HA domain length (e.g. about every 10, 15, 20, 25, 30, 35 or 40 monosaccharides), or some other length below which the resulting LMW-HA domains will function as irreversible acceptors for HC transfer as described above. Methods to substitute tyramine onto HA, as well as to control the substitution rate, are disclosed in the aforementioned patents incorporated by reference. While tyramine is described here as the non-native HA adduct for providing LMW-HA domains, it will be appreciated that other non-native adducts that will not be recognized as native HA by the TSG-6 enzyme can be used.

As will be appreciated from the foregoing, there are at least two modes by which HMW HA can be used to provide a source of LMW-HA domains useful to irreversibly transfer HCs based on the disclosed methods. One mode is to supply a hydrogel that is prepared by cross-linking periodically-substituted moieties along the length of HMW HA (e.g. the TB-hydrogels disclosed in the aforementioned patents), wherein the substitution rate is such that upon breaking down (e.g. digestion via hyaluronidase or free radicals) the hydrogel at an inflammation site, the resulting HA fragments have sufficiently low molecular weight to function as LMW HA in the disclosed methods. A second mode is to supply a periodically-substituted HMW HA macromolecular species not in a cross-linked or hydrogel form, but as free macromolecular strands with period adducts that define LMW-HA domains consisting of 'naked' HA between adjacent adducts. These LMW-HA domains behave as LMW HA to irreversibly transfer HCs via a TSG-6-mediated reaction as discussed above. Both modes can be used to irreversibly quantitatively transfer HCs from tissue HA to LMW HA or LMW-HA domains introduced to the site of inflammation via injection therapy or some other method, thereby reducing or inhibiting the inflammatory process.

It should be noted that in the free-strand modality discussed above, digestion of the free strands is also possible at an inflammation site. However, such digestion will produce LMW HA fragments corresponding substantially to the LMW-HA domains in the substituted HMW HA molecule. Accordingly, these fragments still will function to irreversibly accept HCs transferred from tissue HA according to the disclosed methods.

In addition to treating inflammation, an alternative embodiment involves using LMW HA oligosaccharides as a female contraceptive. The TSG-6 mediated transfer of HC from IαI to HA is required for female fertility as demonstrated by the fact that knock-out mice for either TSG-6 or bikunin, a component of IαI, are infertile. If the LMW HA could be used to prevent HC transfer to the HA in the ECM of the developing cumulus cell-oocyte complex, oocyte maturation could be disrupted and oocyte fertilization and pregnancy prevented. This embodiment provides a non-hormone-based therapy for contraception. The use of LMW HA as a contraceptive as here described may have lower potential for side effects and other risks associated with conventional, hormone-based therapies.

It has been observed that tyramine-substituted (TS) HA can be modified with HC in vitro via recombinant TSG-6 and serum as a source of IαI similar to "naked" HA, and that the resulting HC-decorated TS-HA (hereafter HC-TS-HA) can be subsequently cross-linked with horseradish peroxidase and hydrogen peroxide as described in the above-incorporated patents to form tyramine-cross linked hydrogels of the HC-TS-HA (such hydrogels being referred to herein as HC-TB-HA). These HC-TB-HA hydrogels can be used for various tissue engineering and repair applications wherein the gels are engineered to be patient-specific through the use of a patient's own serum as the source of HC-bikunin. As HC transfer to HA has been implicated in induction of angiogenesis, these HC-TB-HA hydrogels may be useful in those applications in which induction of blood vessels around implanted hydrogel is desirable. For example, in applications involving embedding of cells/tissues in implanted hydrogel constructs (i.e., hydrogel constructs containing fat for facial reconstruction, islet cells as a synthetic pancreas for treatment of diabetes, or ovary tissue as a synthetic ovary). Formation of a capillary bed around the hydrogel construct is desirable as a source of nutrients to feed embedded cells maintaining cell viability.

The disclosed methods and compositions are based on our recent discovery that in the presence of TSG-6, LMW HA of defined size irreversibly displace HCs, a component of the serum-derived proteoglycan, IαI, from HMW HA. The displaced HCs are irreversibly transferred to the LMW HA by action of the TSG-6 enzyme. This provides a paradigm for quantitatively removing pathologic HC ligands from HA of inflamed tissues, potentially alleviating or eliminating inflammation. This will provide not only patient relief from the symptoms of inflammatory disease, but potentially a treatment to prevent or inhibit progression of the inevitable joint (tissue) damage caused by the disease.

A feature of the disclosed methods is that their therapeutic effect has the potential for fewer and less severe side-effects compared to current medications and interventions. In particular, current medications and interventions either treat only the signs and symptoms of the disease, or are designed to slow progression of the disease through modification of immune cell production or function. As expected, these medications have many undesirable side effects including risk of life threatening infections, hematologic issues, kidney and liver damage, severe immunosuppression, death, and long-term effects such as an increased risk of cancer. Our recent discovery of a mechanism whereby the pathological HC-HA matrix in inflamed synovial joints can be restored to a normal, non-inflammatory state through HC transfer to LMW HA provides a mechanistic approach for novel therapeutics and therapies to reduce the signs and symptoms as well as halt the progression of irreversible joint damage in patients by targeting the activating signal for these immune cells rather than the cells themselves.

Conventional medications for treating inflammation work globally to exert their effect directly on a patient's immune cells affecting the patient's inflammatory pathways. As a result, such medications are associated with unwanted side effects such as life threatening infections, hematologic complications such as leucopenia or anemia, and increase risk of malignancy. Conversely, the mode of action for the LMW HA is expected to be more localized and indirect (i.e. not directly altering immune cell function) via removal of the specific matrix signal responsible for attracting and activating immune cells at the inflammatory site. As a result, the use of LMW HA in the treatment of inflammatory disease as disclosed herein may be expected to have lower potential for (and less severe) side-effects compared to conventional treatments.

While the foregoing discussion has been related to HA, it bears noting that materials other than HA may be used to mediate the transfer of HCs, from tissue HA as a treatment for inflammation. For example, it is known that HCs can be transferred by TSG-6 to un-sulfated chondroitin sulfate chains (0S-CS), which have a disaccharide repeat identical to HA except for the conformation of one hydroxyl group. While HA is a better acceptor of HCs from TSG-6 than 0S-CS, the 0S-CS works and presumably would show a similar size dependence relative to the reversibility of the reaction. It may also be that HC-0S-CS is not recognized by immune cells as this is not a natural product driving the immune process. Sulfated CS is reported not to be acceptors for HC transfer by TSG-6, but this could be dependent on the type of sulfation pattern, as the CS chain that is part of bikunin and IαI has both sulfated and un-sulfated disaccharides and does act as a HC acceptor/donor. Other molecules like heparin, heparan sulfate, and alginate may also be possible substitutes for HA or any other molecule containing hexuronic acid residues. Finally, chimeras of glycosaminoglycan chains composed of stretches of HA interrupted with stretches of other glycosaminoglycans such as chondroitin, chondroitin sulfate, heparin, or heparan sulfate could be used to create LMW HA domains within HMW glycosaminoglycan chains similar to that described above for the periodic substitution of HMW HA by adducts such as tyramine.

EXAMPLES

Example 1

Rheumatoid Arthritis (RA) is a chronic, systemic inflammatory disorder affecting more than 1% of the world population, and about 2 million people in the US alone. RA may affect many tissues and organs, but principally attacks synovial joints (SJs). The process produces an inflammatory response of the synovium (synovitis) secondary to hyperplasia of synovial cells, excess synovial fluid (SF), the development of pannus in the synovium, and invasion by white blood cells, which produce a variety of tissue destructive factors. The pathology of the disease process often leads to the destruction of articular cartilage and ankylosis of the joints, a disabling and painful condition, which can lead to substantial loss of function and mobility if not adequately treated. Currently, the cause of RA is unknown, and there is no cure with the only option at end stage disease being total joint replacement. Current medications and interventions either treat only the signs and symptoms of the disease, or are designed to slow progression of the disease through modification of immune cell production or function. As expected, these medications have many undesirable side effects including risk of life threatening infections, hematologic issues, kidney and liver damage, severe immunosuppression, death, and long-term effects such as an increase risk of cancer. Our recent discovery of a mechanism whereby the pathological HC-HA matrix in inflamed SJs can be restored to a normal, non-inflammatory state through HC transfer to LMW HA provides a mechanistic approach for novel therapeutics and therapies to reduce the signs and symptoms as well as halt the progression of irreversible joint damage in RA patients.

We have learned that the formation of the pathological HC-HA complex is a dynamic process whereby TSG-6 readily "swaps" HCs along the HMW HA backbone until reaching equilibrium (FIG. 2A). Importantly, although LMW HA readily serves as an acceptor for HC transfer from HMW HC-HA, it is unable to serve as a HC donor (FIG. 2B) resulting in irreversible transfer of HCs from HMW to LMW HA. Thus, smaller fragments of HA can serve as the basis for anti-inflammatory therapies whereby the pathological HC-HA matrix in inflamed SJ can be restored to a normal, non-inflammatory state via irreversible TSG-6-mediated transfer of HCs from ECM-nascent HMW HA to LMW HA strands. This is the first mechanistic description of a function for LMW HA, which provides the basis for therapies for inflammatory diseases via LMW HA supplements. Unlike current medications, which act directly through modification of immune cell production or function, LMW HA therapy may provide a safer alternative for RA treatment as well as halt the progression of irreversible joint damage in these patients without the unwanted side effects of existing treatments.

Abnormal Heavy Chain Modification of Hyaluronan in Synovial Fluid in Rheumatoid Arthritis.

Hyaluronan (HA) is a large glycosaminoglycan (GAG) in which the disaccharide (glucuronic acid-β1,3-N-acetylglucosamine-β1,4-) is repeated several thousand times (4). It is synthesized at the cell surface of type B synoviocytes, reaching concentrations of 3-4 mg/ml in the SF (5). Its unique physical properties as a high molecular weight (HMW), anionic, structural carbohydrate confer its ability to function as a hydrated, viscoelastic lubricant for the SJ. Under normal conditions, it exists as a "naked" glycosaminoglycan, lacking a covalent bond to any protein. During joint inflammation, this relatively inert HA matrix is transformed into a ligand for inflammatory cell receptors via the covalent transfer of heavy chains (HCs) from inter-α-inhibitor (IαI) via TSG-6 protein.

Figure 10:
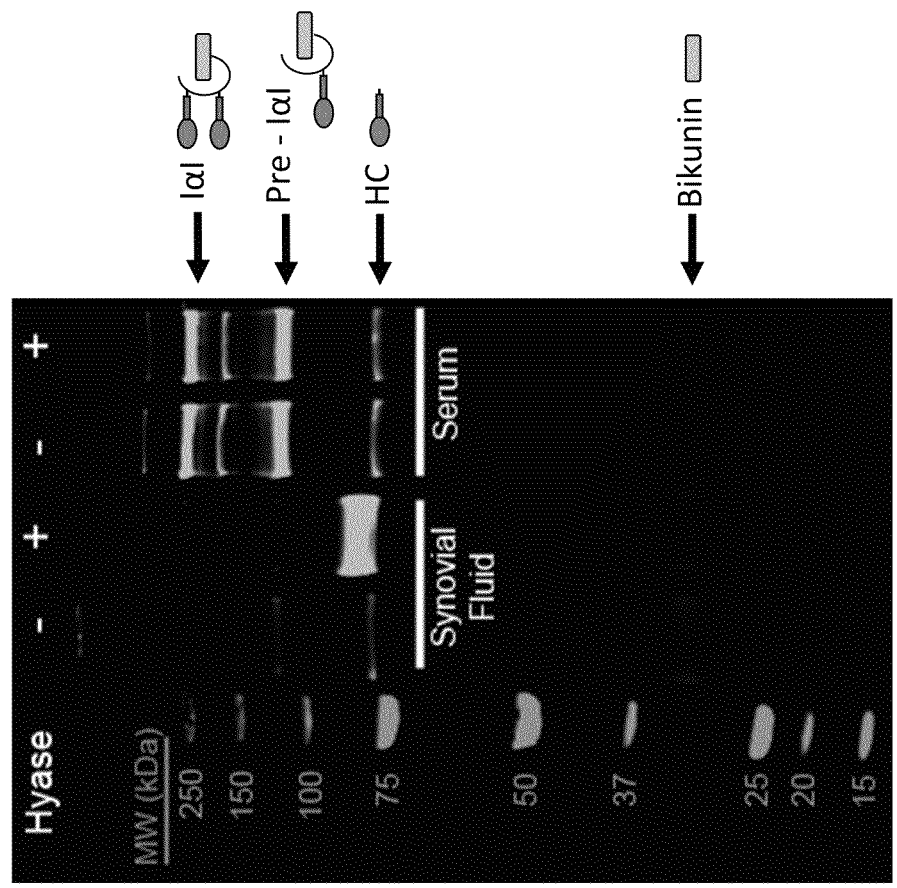
FIG. 10 shows an analysis of heavy chain complex in synovial fluid from rheumatoid arthritis patients, by Western blot.

This has been shown experimentally, as follows (FIG. 10). Synovial fluid (SF) and serum from a patient with rheumatoid arthritis (RA) were treated +/−hyaluronidase (hyase) and analyzed by Western blot, probing the blot with a polyclonal antibody that has reactivity against the heavy chains (HC) and bikunin of the tri-peptide inter-α-inhibitor (IαI). Hyaluronidase treatment of SF released heavy chains bound to hyaluronan so that they ran as a distinct 83 kDa band on the gel. This did not occur when serum was treated with hyaluronidase, confirming the absence of the HC-HA complex in this patient's serum. In serum, heavy chains (83 kDa) are linked to bikunin (37 kDa) via a chondroitin sulfate glycosaminoglycan to form a tri-peptide (IαI) or a di-peptide (pre-IαI).

In 1965, Sandson, et al, first reported that HA from pathological SF was associated with the components of IαI (6). In 1999, this association was identified as a covalent bond between the HCs of IαI and HA (7). IαI is a serum proteoglycan, synthesized by hepatocytes in the liver, and secreted into the circulatory system where it reaches relatively high concentrations (0.15-0.5 mg/ml) (8). It is composed of 3 polypeptides: the trypsin inhibitor called bikunin, (16 kDa) and two HCs (~83 kDa each) (9). The two HCs are covalently attached to bikunin's single chondroitin sulfate (CS) chain by an ester linkage between a HC aspartate and the 6-OH of galNAc in the CS. Under normal conditions, IαI is absent from SF since the synovial barrier prevents proteins larger than 100,000 kDa from entering the synovial space (6), but during inflammation, IαI leaks into the synovial space through dilated capillaries where it serves as a HC donor for the transfer of HCs to HA via the enzyme TSG-6.

TSG-6 is a 35 kDa protein that is synthesized and secreted by many cells after treatment with tumor necrosis factor alpha (TNFα) and interleukin 1 (10). TSG-6 binds to HA via its link module and can form a HC-TSG-6 complex with the HCs of IαI (FIG. 1) (11). Through our investigations, and others, we identified TSG-6 as the enzyme responsible for the covalent transfer of HCs to HA (12-14). Elevated levels of TSG-6 have been observed in asthmatic bronchoalveolar lavage fluid (15), in the airway epithelium and secretions of smokers (15), and in infarcted regions following stroke (16). The covalent transfer of HCs from IαI via TSG-6 transforms the HA matrix into a ligand for inflammatory cell receptors. This was illustrated in a study which isolated the HC-HA complex from inflamed SF and showed that leukocytes preferentially bound to the HC-HA complex when compared to HA alone (17). Similarly, our own studies have shown that the artificial addition of HCs to HA "cable" structures via the addition of recombinant TSG-6 significantly enhanced leukocyte adhesion (not shown). The white blood cell count from inflamed SF are 10-500 fold above normal levels, driving inflammation in this joint. The HC-HA complex functions as a specific ligand for these inflammatory cell receptors, providing a "sticky" platform for adhesion within this viscoelastic fluid. The resolution of inflammation in RA and other inflammatory conditions should, at least partially, involve a restoration of the HA matrix in SF to its original state, unmodified from HCs.

Irreversible Transfer of Heavy Chains to Low Molecular Weight Hyaluronan via TSG-6.

We have discovered a mechanism whereby LMW HA could function in the clearance of HCs from HC-HA matrices in SF. This involves a unique ability for LMW HA to serve as an irreversible HC acceptor from HMW HA via transfer by TSG-6. Results were as follows.

Figure 7A:
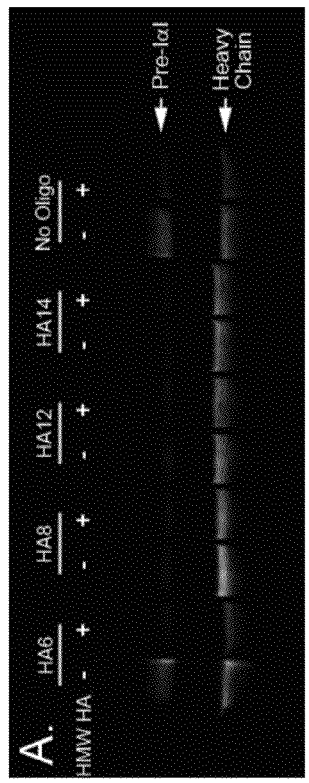
FIG. 7 illustrates results of a preliminary range study for the irreversible transfer of heavy chains to hyaluronan oligosaccharides, in which Western blots show the molecular weight gel shift of heavy chains (HCs) transferred from inter-α-inhibitor (IαI) and pre-IαI to hyaluronan (HA) and swapping between HA molecules to HA oligosaccharides. (A) Western blot with mouse serum. (B) Western blot with human serum.
Figure 7B:
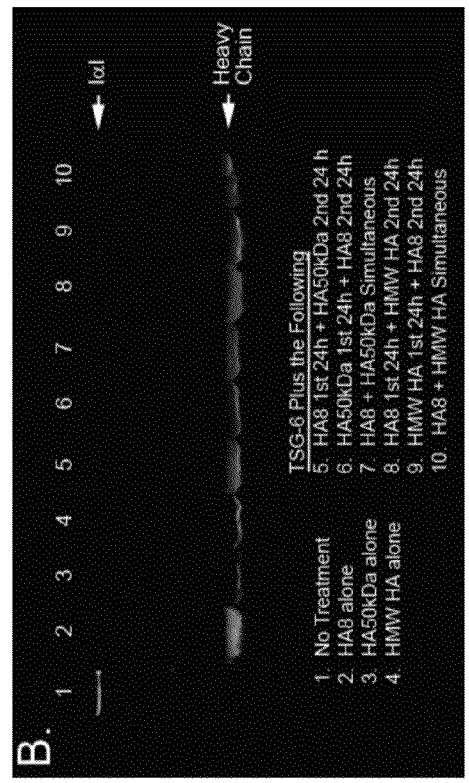

A preliminary range study for the irreversible transfer of heavy chains to hyaluronan oligosaccharides revealed molecular weight gel shifts of heavy chains (HCs) transferred from inter-α-inhibitor (IαI) and pre-IαI to hyaluronan (HA) and swapping between HA molecules to HA oligosaccharides (FIG. 7). Results from Western blots with mouse serum show that HA6 (and presumably <HA6) are not HC acceptors or donors, that HA8-14 can serve as HC acceptors but not donors, and that HMW HA (~1500 kDa) can be both a HC acceptor and donor (FIG. 7A). Results with human serum show that HA having about 160 monosaccharide (~30 kDa HA) functions like HMW HA (~1500 kDa) as both a HC acceptor and donor, unlike HA8 which is only a HC acceptor (FIG. 7B). These data establish HA8 as the lower HA (composed of complete disaccharide units) size limit for irreversible HC transfer and show that the upper limit is below about 30 kDa HA. These experiments were repeated 2 times.

Figure 8A:
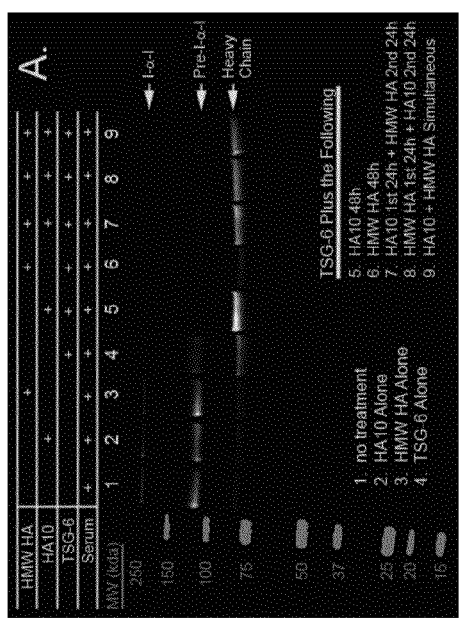
FIG. 8 shows results of irreversible transfer of heavy chains from HMW HA to LMW HA via TSG-6. (A) Western blot showing the molecular weight gel shift of HCs transferred from inter-α-inhibitor (IαI), pre-IαI, or HMW HA to LMW HA. (B) Quantification of the HC band from the Western blot, in which error bars represent standard deviation (n=3).
Figure 8B:
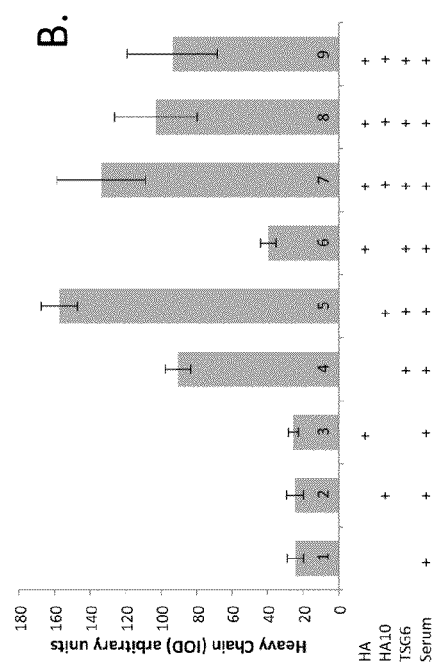
Figure 9B:
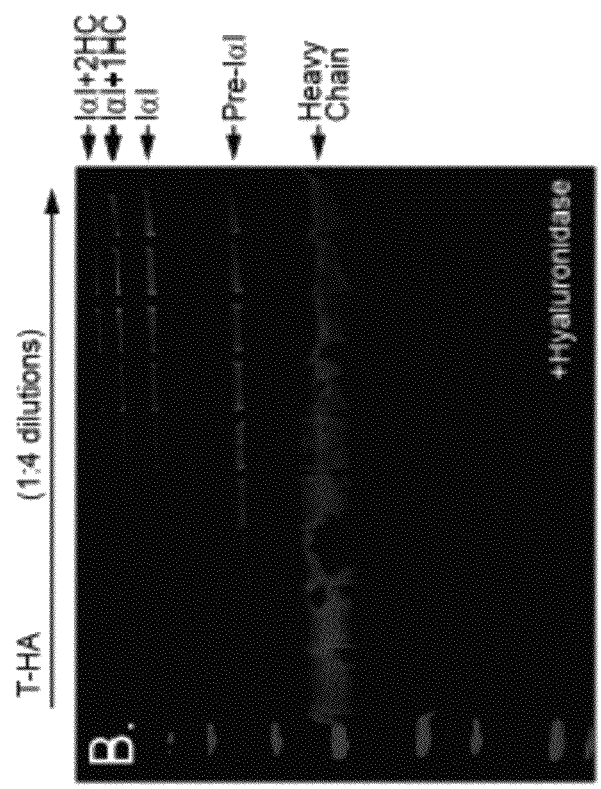
FIG. 9 shows modification of tyramine-substituted hyaluronan (T-HA) with heavy chains (HC) from inter-α-inhibitor (IαI) via TSG-6, by Western blot. (A) Modification of HA, followed by hyaluronidase treatment. (B) Modification of T-HA, followed by hyaluronidase treatment. (C) Modification of HA, without subsequent hyaluronidase treatment. (D) Modification of T-HA, without subsequent hyaluronidase treatment.
Figure 9A:
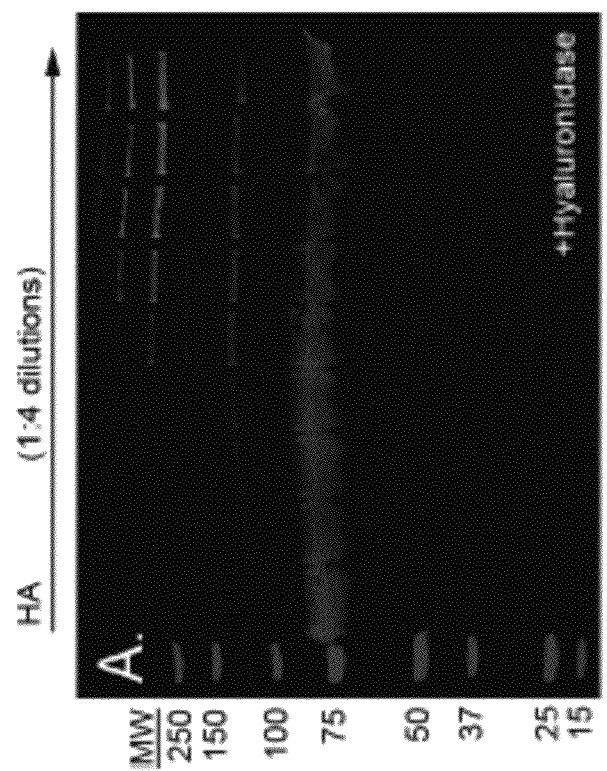
Figure 9D:
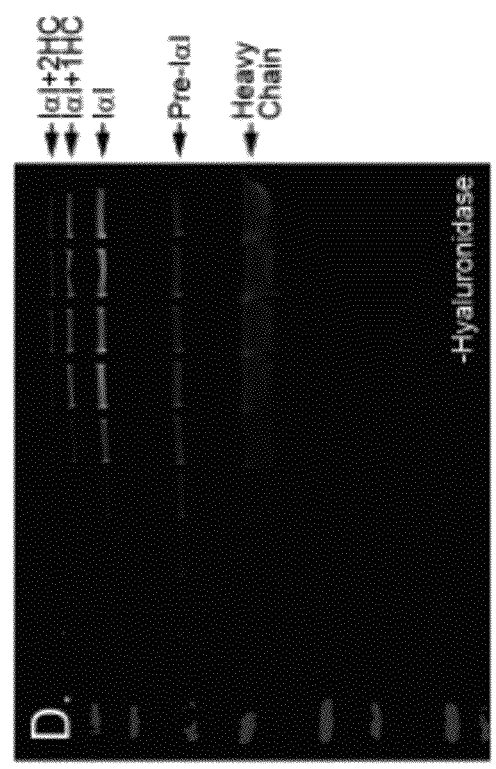
Figure 9C:
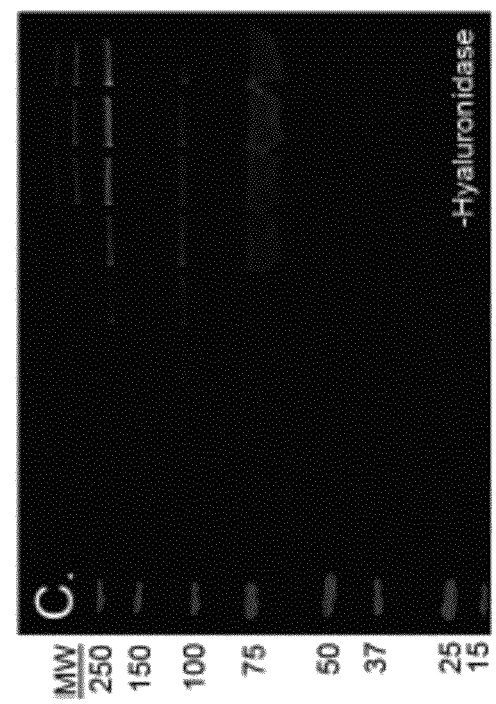

An additional study revealed irreversible transfer of heavy chains from HMW HA to LMW HA via TSG-6 (FIG. 8). Results from a Western blot show the molecular weight gel shift of HCs transferred from inter-α-inhibitor (IαI), pre-IαI, or HMW HA to LMW HA (FIG. 8A). Quantification of the HC band from the Western blot is also shown, in which error bars represent standard deviation (n=3) (FIG. 8B).

Considering FIG. 8A in more detail, lanes 1-3 show that HCs are present in serum as part of the IαI or pre-IαI complexes. This is unaffected by the addition of LMW HA 10 monosaccharides long (HA10) (lane 2) or by the addition of a HMW HA ~1600 kDa (lane 3). In lane 4, serum supplemented with TSG-6 results in release of free HCs from IαI and pre-IαI. Supplementation of this serum with additional LMW HA (i.e. HA10) in the presence of TSG-6 causes a gel shift of the HC from IαI and pre-IαI (comparing lane 5 with 4). When the serum is supplemented with HMW HA instead of LMW HA in the presence of TSG-6 (lane 6), most of the HC fail to enter the gel because their attachment to HMW HA makes the HC-HA complex too large for resolution on this gel. In lane 7, HC from serum were transferred to HA10 for the first 4 hrs and then the reaction mixture was spiked with equivalent amounts of HMW HA for the remaining 24 hrs (48 hrs total). Since the HC gel shift is identical to the addition of HA10 alone (as seen in lane 5), this implies that once transferred to HA10, the majority of HC remain attached to this HA oligosaccharide even in the presence of HMW HA. However, the reverse of this does not occur (lane 8). In this instance, HC were transferred to HMW HA in the first 24 hrs, and then the reaction mixture was spiked with equivalent amounts of HA10 for the remaining 24 hrs (48 hrs total). This resulted in a HC gel shift identical to lane 7, implying that the HC were transferred from HMW HA to HA10 in an irreversible manner. Similarly, when serum was supplemented with HMW HA and HA10 in the presence of TSG-6 simultaneously for 48 hrs (lane 9), the majority of HC demonstrated a gel shift indicative of transfer to HA10 alone. These data demonstrate that TSG-6 "swaps" HCs between HA molecules in a size dependent manner which is reversible for HMW HA, but irreversible for LMW HA, proving that LMW HA can function as an irreversible acceptor for HC derived from HMW HC-HA.

Accordingly, we have learned that TSG-6 readily "swaps" HCs between HA molecules of HMW HA. Although LMW HA can serve as a HC acceptor, it is unable to serve as a HC donor, thereby making the reaction irreversible. This can be explained in the following model. In order for HC transfer to LMW HA to occur, the TSG-6-HC intermediate must bind LMW HA via the HA binding "link" domain of TSG-6 and transfer the HC to LMW HA. Without wishing to be bound by theory, it is believed that once the HC is transferred, steric hindrance by the attached HC prevents TSG-6 from being able to bind the HA portion of LMW HC-HA, thereby preventing removal of its HC (FIG. 3).

Figure 11:
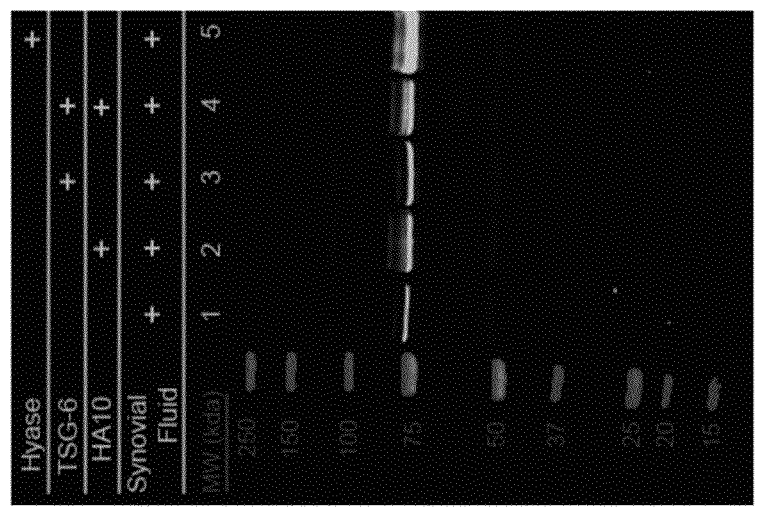
FIG. 11 shows results of irreversible transfer of heavy chains from HMW HA to LMW HA in the synovial fluid of rheumatoid arthritis patients, by a Western blot of SF probed with an antibody that binds only heavy chains (HCs).

Evidence that this process can be applied to human SF to remove HCs from HMW HA via irreversible transfer to LMW HA includes the following (FIG. 11). A Western blot of SF probed with an antibody that binds only heavy chains (HCs) is shown. Free HC, or HC bound to LMW HA, is present in SF from an RA patient (lane 1). When LMW HA containing a HA fragment of 10 monosaccharides (HA10) was applied to this SF, endogenous TSG-6 transferred HCs from HMW HC-HA onto HA10 (compare lanes 1 and 2), causing a ~1.6 kDa shift higher in MW. When both exogenous TSG-6 and HA10 are applied to the SF (lane 4), HCs from HMW HC-HA are transferred to HA10 in an irreversible manner. This induced a 1.6 kDa vertical gel shift similar to lane 2, albeit the intensity of the band is stronger with the addition of exogenous HA10. Treatment of SF with hyaluronidase (hyase) released all the HCs bound to HMW HA (lane 5), showing that the addition of more HA10, or more time, would be required to completely remove all of the HCs from HMW HA. These data demonstrate a mechanism whereby HCs are removed from HMW HA, and transferred to LMW HA, in SF from RA patients.

Role for Low Molecular Weight Hyaluronan in the Removal of Heavy Chains from High Molecular Weight Hyaluronan in the Synovial Fluid of Rheumatoid Arthritis Patients.

In the synovial cavity, HA degradation into smaller fragments is most likely to occur via hyaluronidase digestion by phagocytic cells (i.e. macrophages) and by oxidative damage via reactive oxygen species (released by neutrophils) (18). We now know that these fragments have the ability to serve as irreversible acceptors of HCs derived from HMW HC-HA (FIG. 8).

Figure 12:
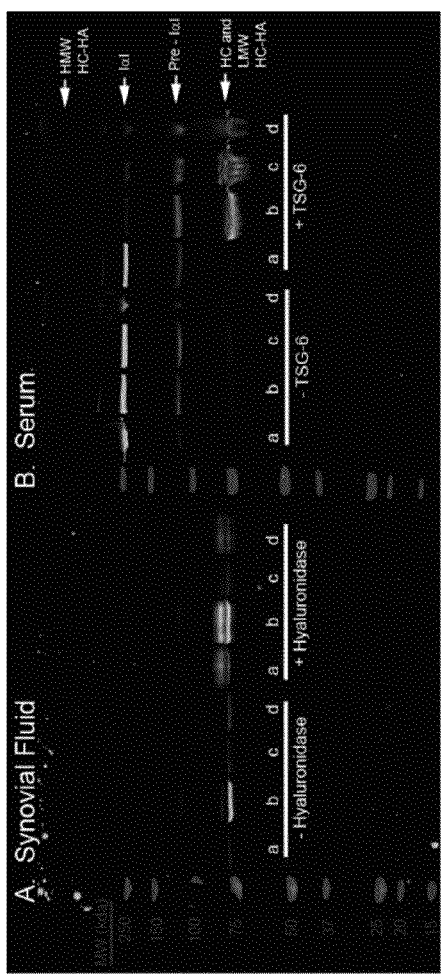
FIG. 12 shows evidence for LMW HA in synovial fluid and serum from rheumatoid arthritis patients. (A) Synovial fluid (SF) from four patients (a-d) was treated +/− with hyaluronidase and the amount of released HCs analyzed by Western blot. (B) Serum from these same patients was treated α/− with TSG-6 (panel B).
Figure 13:
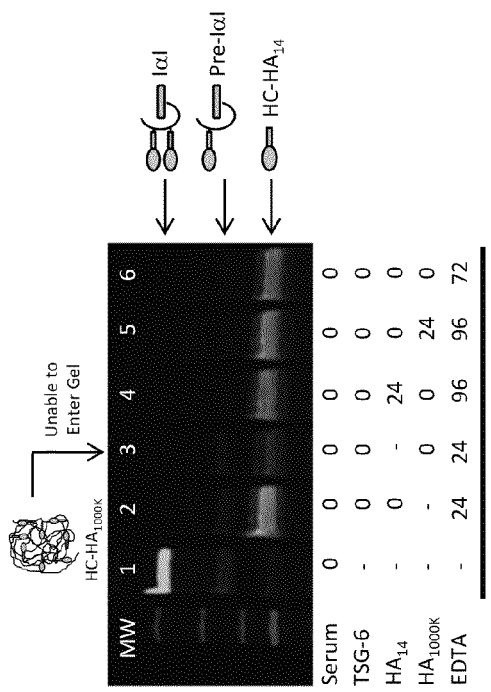
FIG. 13 shows results for irreversible transfer of human serum heavy chains to hyaluronan oligosaccharides, by Western blot.

In addition to the LMW HA fragments that are locally produced as a degradation product of HMW HA in SF, our data suggest that serum from tested RA patients contained relatively high levels of circulating LMW HA (FIG. 12). Specifically, synovial fluid (SF) from four patients (a-d) was treated +/− with hyaluronidase and the amount of released HCs analyzed by Western blot (panel A). Serum from these same patients was treated +/− with TSG-6 (panel B). This transferred HCs from IαI onto circulating LMW HA, or alternatively, TSG-6 released free HCs. Free HC and HC bound to LMW HA (doublet above the main HC band) were present in all SF (panel A). Hyaluronidase treatment of SF released HCs bound to HMW HA. HMW HC-HA was also observed in serum as a smear at the top of the gel (panel B; notice patients a & d). This was not seen in the SF because the HMW HA in SF is apparently larger than in serum. Treatment with TSG-6 caused a strong gel shift of the HCs from IαI with patient "b" to form a HC smear indicative of transfer to LMW HA. This also was prominent with patients "c" and "d." TSG-6 treatment of patient "a" removed HCs from HMW HA to LMW fragments. Furthermore, the appearance of a HMW HC-HA smear with patient "c" implies that there was circulating levels of "naked" HMW HA in this patient. These data show that the HCs are bound to both HMW and LMW HA in SF of RA patients, with HMW HC-HA predominating. Relatively high levels of LMW HA were found in the serum from RA patients, which could serve as an irreversible acceptor of HCs from HMW HC-HA.

Based on the above, we propose a therapy whereby LMW HA is administered locally at the site of inflammation (with or without exogenous or endogenous TSG-6 enzyme and/or IαI) to serve as an irreversible acceptor for HCs and a modulator of the pathological HC-HA complex in the SF of inflamed SJs. Note that exogenous or endogenous TSG-6 and/or IαI could be supplied in a bolus together with the LMW HA to supplement the enzyme and IαI already present at the site, or to provide those species in an inflammation site where they may be naturally deficient.

The Size Range Whereby LMW HA can Function as an Irreversible Acceptor of HCs.

HMW HA can both accept and donate HCs as they are "swapped" between HA molecules via the enzyme TSG-6 (FIGS. 2B and 7). Interestingly, a HA fragment of 10 monosaccharides (HA10) was able to accept HCs from HMW HA via TSG-6, but once bound, the enzyme was unable to use HC-HA10 as a HC donor (e.g. FIGS. 8 and 11). Moreover, HA molecules having between 8 and 14 monosaccharide units have been found to perform suitably as acceptors for TSG-6-mediated HC attachment while not permitting the reverse reaction to remove HCs from the HA molecules (via TSG-6) once attached. While HA8-14 molecules have performed suitably in this regard to provide irreversible attachment of HCs transferred via TSG-6 from HMW HA, lower molecular-weight HAs having six or fewer monosaccharide units did not work in our experiments. Without wishing to be bound by theory, it is believed that these small HA molecules did not possess sufficient length to accommodate a TSG-6 binding site necessary to initiate TSG-6-mediated HC-transfer to the HA molecule. Similarly, based on our theory of steric hindrance-irreversible HC-transfer from HMW to LMW HAs, suggests there will be a threshold HA length beyond which the molecule will have sufficient length to accommodate a TSG-6 binding site while HCs are attached. At this threshold length, the HA will no longer serve as an effective LMW HA in the disclosed methods and therapies for quantitatively transferring HCs from ECM-nascent HMW HA. Our experiments suggest that this threshold HA length is about 160 monosaccharide units or greater. The LMW HA molecules used in the disclosed methods and therapies preferably has a length in the range of about 8-25 monosaccharide units, 8-20 monosaccharide units, 8-15 monosaccharide units or 8-10 monosaccharide units. Assigning a biological function to a distinct range of HA sizes may be relevant in the treatment of different inflammation syndromes in different tissues because the size of HA varies by tissue type and stage of inflammation (18).

Clearance of LMW HA and HC-HA in the Synovial Fluid.

SF is not a static pool, but is continually being absorbed and replenished by the synovial lining of the joint cavity (19). Raw SF is formed as plasma diffuses from synovial capillaries, into the interstitial matrix, and across the fenestrated membranes of type B synoviocytes into the synovial cavity. Subsequently, synoviocytes secrete macromolecules such as hyaluronan and the proteoglycan lubricin into the raw serum exudate. SF is absorbed back through the fenestrated membranes and the interstitial matrix of the synovium and into the synovial venous and lymphatic system where it is returned to the circulatory system to be cleansed by the liver and kidneys (20).

Several studies have shown that there is a disparity between the turnover of macromolecules in SF, implying selective permeability of the synovial membrane (3, 21-22). For example, the turnover of water and albumin in rabbit and human knees is about 1-2 hr (21-22). In contrast, the half-life of HMW HA is an order of magnitude slower, ranging from 15-28 hrs (22-24). The turnover of HA in SF is a function of its size, with lower molecular weights presenting shorter half-lives (3). Since the covalent transfer of HCs (83 kDa) to HMW HA in SF during inflammation would increase its accumulative MW, we predict that the turnover of HMW HC-HA would be even longer than naked HMW HA alone. In contrast, we expect that the turnover of HA10 (1.6 kDa) and HC-HA10 (85 kDa) in SF would resemble that of water and albumin (67 kDa). These are important distinctions because they could explain the means whereby the pathological HC modification of HMW HA could be flushed out of SF via their irreversible transfer to LMW HA.

Of note, while previous studies have shown that HMW HA is rapidly cleared from the circulatory system via the liver (20), this may not be true for LMW HA in the size range that can function as an irreversible acceptor for HCs and the effect that the HC modification might have on this process is unknown.

Summary.

We have identified a novel mechanism whereby LMW HA can function as an irreversible acceptor to restore HC modified matrices in inflamed SJs to their original state.

Example 2

Irreversible Transfer of Heavy Chains to LMW HA Via TSG-6

Conventional RA therapies, such as corticosteroids and disease-modifying anti-rheumatic drugs (DMARDS) treat only the signs and symptoms of the disease, or slow its progression through modification of immune cell production or function. These treatments globally affect the immune system with serious long-term side effects. In contrast, the compositions and methods disclosed herein rely on a mechanism whereby relatively small HA molecules can be used to remove HCs from HC-HA matrices in SF, thereby restoring them to their normal (naked) state. This technology is based upon the observation that while TSG-6 reversibly swaps HCs between large HA molecules found in SF, HC swapping to smaller HA molecules is irreversible. In other words, while large HA molecules are both HC acceptors and donors, smaller HA molecules are only HC acceptors.

For example, results from a Western blot show irreversible HC "swapping" from HA1000K (high molecular weight HA with a molecular weight of 1000 kDa, also termed $HA_{1000kDa}$) to HA14 (HA oligosaccharide containing 14 monosaccharides) via recombinant TSG-6 (FIG. 13). The HCs of IαI from human serum (lane 1) are completely transferred to HA14 (lane 2) and to HA1000K (lane 3) in 24 hours. Note that HCs transferred to HA1000K do not enter the gel because the HC-HA complex is too large, thus giving the appearance that they disappeared. In lane 4, HCs were first transferred to HA1000K for 24 hours, after which the reaction mixture was spiked with HA14 to allow swapping of HCs from HA1000K to HA14 for 72 hours. In lane 5, the reverse sequence was applied (i.e. transfer of HCs to HA14 for first 24 hours followed by incubation for 72 hours with HA1000K for 72 hours). Notice that while the HCs were able to swap from HA1000K to HA14 (lane 4) the reverse of this did not occur (lane 5). Thus, transfer of HCs to HA14 is an irreversible event. This is further illustrated in lane 6 in which both HA1000K and HA14 were applied simultaneously for 72 hours. Thus, while HA1000K is both a HC acceptor and donor, HA14 is exclusively an irreversible HC acceptor. Similar results were obtained with mouse serum.

This phenomenon can be exploited to remove HCs from pathological HC-HA matrices found in RA and other inflammatory diseases, thereby making HA less sticky by removing the HC-HA ligand by which inflammatory cells adhere to HA matrices (FIG. 14). Thus, for example results from a Western blot show irreversible transfer of heavy chains from mouse synovial fluid hyaluronan to hyaluronan oligosaccharides, including evidence for irreversible HC transfer from HMW HC-HA to HA14 oligosaccharides as well as evidence of endogenous SF TSG-6 activity in SF derived from mice subjected to RA is provided. In lanes 1-2, SF was treated with and without hyaluronidase for 72 hours. In lane 4, in the presence of exogenous recombinant TSG-6, HCs from HMW HC-HA were irreversibly transferred to HA14 oligosaccharides. In lane 3, in the absence of exogenous TSG-6, HC transfer to HA14 occurred as a result of endogenous SF TSG-6 activity. Similar results were obtained with human SF derived from RA patients (not shown).

Example 3

Size-Range Study of Irreversible Heavy-Chain Transfer I

We have learned that the size range for irreversible HC transfer to HA is from 8 monosaccharides (corresponding to about 1.5 kDa) to at least 87 monosaccharides (corresponding to about 16 kDa). Evidence includes the following (FIG. 15). Recombinant TSG-6 covalently transferred HCs from serum derived IαI (lane 1) to different sizes of HA polysaccharides (lanes 2-9) for 4 hrs at 37° C. to form the HC-HA complex with these polysaccharides. Afterwards, HA1000K was added to an aliquot of these samples for 24 hrs (+) (lanes 3,5,7,9), or HA1000K was not added (−) (lanes 2,4,6,8). In this experiment, the HAs ranged in size from HA14 (i.e. 14 monosaccharides, corresponding to 2.66 kDa) (lanes 2,3) to HA87 (i.e. 87 monosaccharides, corresponding to 16.48 kDa) (lanes 8,9). The data show that once HCs were transferred to these HAs ranging from 3-16 kDa, TSG-6 could not remove the HCs to transfer them to HA1000K.

Actual numbers for HA molecular weight and calculated monosaccharides based on the MALLS-SEC analysis by Hyalose are provided (FIG. 15). Quantitation of this gel indicated that the (+) bands were approximately 20% less than the (−) bands for $HC\text{-}HA_{2.66kDa}$, $HC\text{-}HA_{7.05kDa}$, and $HC\text{-}HA_{10.70kDa}$, and approximately 40% less for $HC\text{-}HA_{16.48kDa}$. Thus the 4 hour incubation required to transfer all of the HCs from the IαI to the HA polysaccharides was insufficient to allow all of the HC-HA formed to be at irreversible sites on the HA polysaccharides.

When the initial transfer of HCs from the IαI to the HA polysaccharides is allowed to incubate for 24 hrs at 37° C. before addition of the competing polysaccharide (HA1000K), it appears all of the HC transfer has shifted to irreversible sites on the polysaccharides (FIG. 16). Specifically, recombinant TSG-6 covalently transferred HCs from human serum derived IαI (lane 2) to different sizes of HA polysaccharides (lanes 3-10) for 24 hrs at 37° C. to form the HC-HA complex with these polysaccharides. After this initial 24 hrs, HA1000K was added to an aliquot of these samples for 24 hrs (+) (lanes 4,6,8,10) or HA1000K was not added (lanes 3,5,7,9). The data show that once HCs were transferred to HA57 (i.e. 57 monosaccharides, corresponding to 10.70 kDa) (lanes 3,4,7,8) or HA87 (i.e. 87 monosaccharides, corresponding to 16.48 kDa) (lanes 5,6,9,10), TSG-6 could not remove the HCs to transfer them to HA1000K (HC-HA1000K is too large to enter the gel).

A further experiment also showed that HA8 to HA21 can serve as irreversible HC acceptors (FIG. 17). Specifically, recombinant TSG-6 covalently transferred HCs from human serum derived IαI (A,B: lane 2) to different sizes of HA polysaccharides (A,B: lanes 3-9) for 2 hrs at 37° C. to form the HC-HA complex with these polysaccharides. After this initial 2 hrs, HA1000K was added to an aliquot of these samples for 24 hrs (+) (A,B: lanes 3,5,7,9) or HA1000K was not added (+) (A,B: lanes 2,4,6,8). The data show that once HCs were transferred to HA containing 8, 10, 12, 14, 18 and 21 monosaccharides (A: lanes 6,7; A: lanes 8,9; B: lanes 2,3;

B: lanes 4,5; B: lanes 6,7; B: lanes 8,9; respectively), TSG-6 could not remove the HCs to transfer them to HA1000K (HC-HA1000K is too large to enter the gel). The HA4 and HA6 data are complicated. In the absence of any HA of a size that can accept HCs, i.e. HA4 and HA6, TSG-6 is able to slowly, but quantitatively, release free HCs over 24 hrs. For the HA4 and HA6, the small amount of free HC band seen upon addition of HA1000K after the initial 2 hr incubation is the result of free HCs generated by TSG-6 in the first 2 hrs in the absence of HA acceptor when no HA1000K is present. The remainder of IαI HC is transferred to the HA1000K over the next 24 hrs. Thus, it is believed that HA polysaccharides from 1.53 to 16.48 kDa (HA8 to HA87) serve as irreversible HC acceptors.

Based on the foregoing, we have determined that HA polysaccharides from 1.53 to 16.48 kDa (HA8 to HA87) are irreversible HC acceptors.

Moreover, as noted above, we have also determined that transfer of HCs to HA that is 30.6 kDa is reversible. Thus, the transition between reversibility and irreversibility lies between HA that is 16 and 30.6 kDa.

Example 4

Heavy Chain Isotypes

Figure 18:
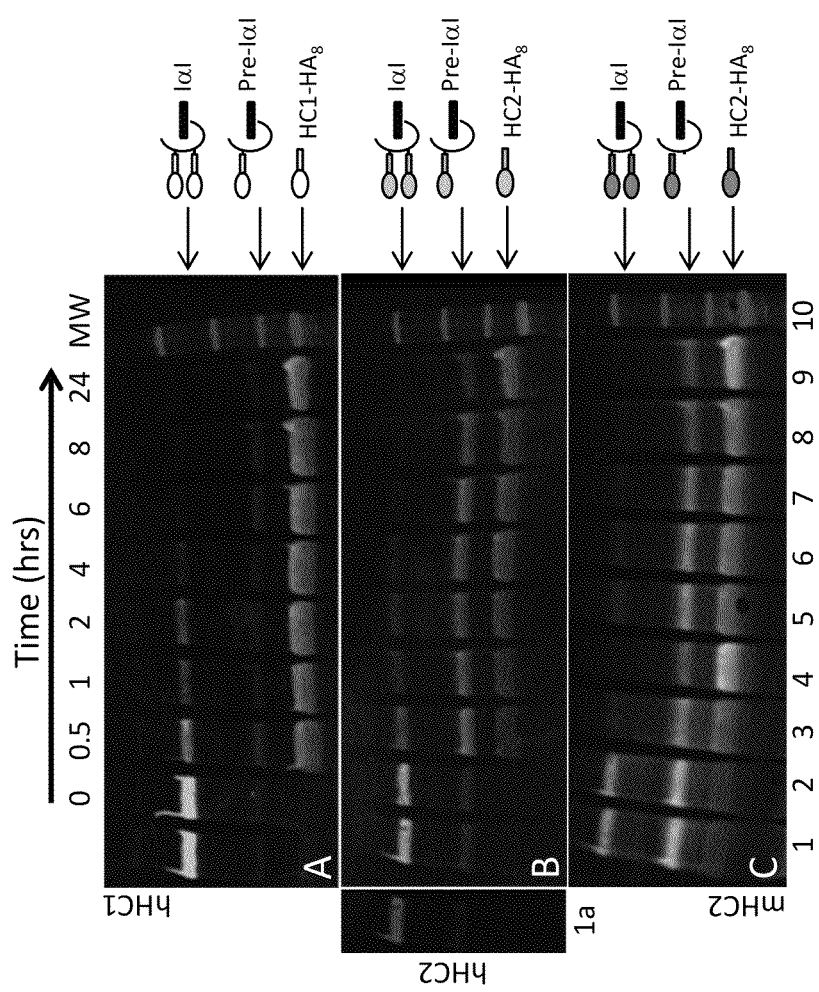
FIG. 18 shows results of kinetics of transfer of serum heavy chains 1 and 2 to hyaluronan oligosaccharides, by Western blot. (A) Human HC1. (B) Human HC2. (C) Mouse HC2. Molecular weight (MW) markers are 75, 100, 150, 250 kDa.
Figure 19:
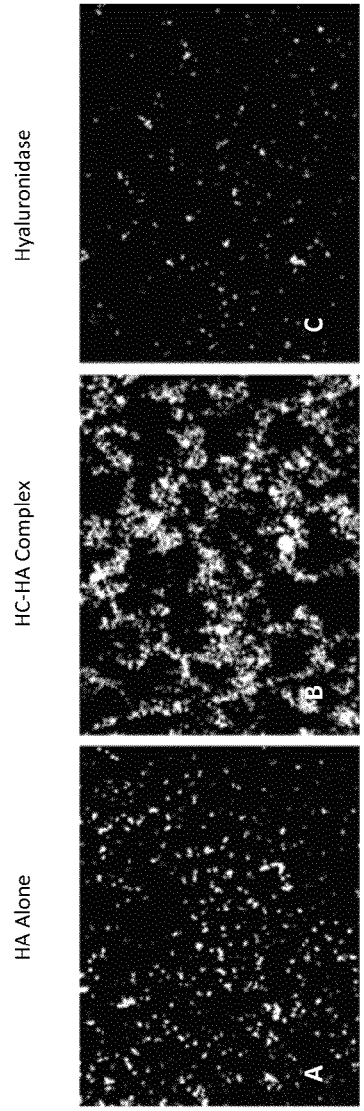
FIG. 19 shows results of heavy chain-hyaluronan complex promoting inflammatory cell adhesion. The HA-HC complex (B), in contrast to HA alone (A), promoted leukocyte adhesion. This adhesion was disrupted by digestion of the HC-HA complex with hyaluronidase (C). Similar results were observed from HC-HA isolated from the synovial fluid of rheumatoid arthritis patients (17).
Figure 20:
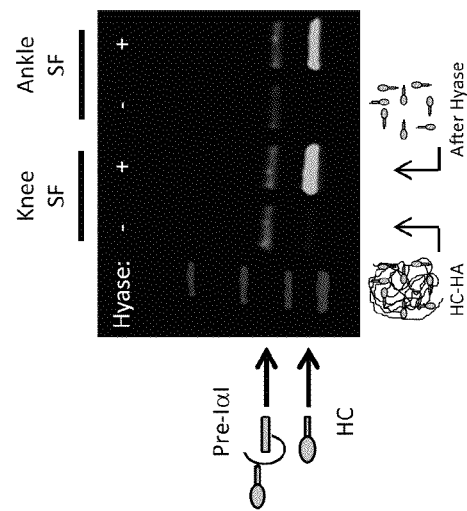
FIG. 20 shows analysis of heavy chain-hyaluronan complex in mouse proteoglycan-induced arthritis synovial fluid (PGIA SF), by Western blot. Molecular weight (MW) markers are 75, 100, 150, 250 kDa.

Five different homologous HCs (HC1-5) are present in two gene clusters mapped to different chromosomes (HC1, 3 and 4 to chromosome 3 and HC2 and 5 to chromosome 10). HC4 is unique in that it is not part of IαI, is not transferred to HA, and is secreted as a free HC. We have shown that IαI in mice and/or humans is comprised of at least 3 different HC isotypes (HC1, HC2 and HC3) (FIG. 18 shows this for HC1 and HC2; HC3 was also confirmed, but not shown).

Specifically, Western blots showing the kinetics of HC1 (A) and HC2 (B,C) transfer from human (A,B) and mouse (C) serum-derived IαI and pre-IαI to HA8 (eight monosaccharides long) via the addition of recombinant TSG-6 are provided (FIG. 18). Transfer of HC1 from IαI in human serum to HA8 was relatively rapid (2-4 hrs), and did not result in the accumulation of the pre-IαI intermediate (panel A). In contrast, transfer of HC2 from IαI in human serum to HA8 was relatively slow (≥24 hrs), and resulted in the accumulation of the pre-IαI intermediate (panel B). Similarly, transfer of HC2 from IαI and pre-IαI in mouse serum to HA8 was also slow (≥24 hrs, panel C). Whereas IαI was the predominant HC-donor in human serum, mouse serum contained predominantly pre-IαI with IαI as a minor component. We have observed this in multiple subjects (not shown). The relative molecular weights of IαI and pre-IαI for human HC1 (A) and HC2 (B) show that HC2 is about 10 kDa larger than HC1. The IαI and pre-IαI bands from HC2 are about 20 kDa and 10 kDa larger than the IαI and pre-IαI bands of HC1. This implies that the IαI may be a homodimer (HC1-HC1 or HC2-HC2) instead of a heterodimer (HC1-HC2). Since HC transfer of HC1 is faster than HC2, HC2 transfer from pre-IαI is not simply the result of slower transfer from pre-IαI than IαI, but is HC specific. HC1 staining was completely absent in mouse serum (not shown). HC3 was found in mouse, but not human serum, albeit possibly because the antibody did not recognize human antigen (not shown). The effects that differential kinetics and the species-predominance of HC isotypes have on the development of RA, and other inflammatory diseases, is unknown.

The presence of HC5 in IαI has not been reported, but we have no reason to believe it is not part of IαI.

It has been suggested that IαI is a heterodimer of two different HCs (HC1-HC2) (27). We have reason to believe that homodimers (HC1-HC1 or HC2-HC2) predominate, since this is the most natural interpretation of the 20 and 10 kDa gel shifts between IαI and pre-IαI (respectively) (FIG. 18). While we cannot conclude from the relative staining of HC1 and HC2 that HC1 predominates in humans while HC2 predominates in mice, it at least raises this possibility. This is an important distinction because our data show that the transfer of HC1 by TSG-6 is significantly faster than the transfer of HC2 to HA (FIG. 18). We also found that IαI predominates in human blood while pre-IαI (lacking one of the two HCs) predominates in mouse blood (FIG. 18). Whether this species-specific difference in the HC composition of IαI has an effect on the onset and progression of RA is unknown.

Example 5

Intra-Articular Injections of HA16K and HA50K in Rabbits Subjected to Mono-Articular RA We hypothesize that injection of HA16K (an irreversible HC acceptor having a molecular weight of approximately 16 kDa) into the inflamed joint will result in the covalent transfer of HCs from pathological HC-HA to HA16K via endogenous TSG-6. We also hypothesize that removal of HCs from HC-HA in the matrix of the joints will cripple this novel extracellular-matrix-based leukocyte retention mechanism, thereby decreasing inflammation in the joint.

A method has been developed to test this hypothesis. In accordance with this method, intra-articular injections of HA16K (only a HC acceptor, having a molecular weight of 16 kDa) and HA50K (both a HC acceptor and donor, having a molecular weight of 30.6 kDa as determined by MALLS-SEC) into rabbits subjected to mono-articular RA using the methylated BSA model of antigen-induced-arthritis (AIA) are carried out. The effect that HA16K has on relieving joint swelling and inflammation compared to HA50K which functions as a negative control is compared. The method is as follows.

Manufacture Gram-Scale Quantities of Hyaluronan (HA) That are Both Reversible (HA50K) and Irreversible (HA16K) Heavy Chain (HC) Acceptors.

HA16K and HA50K polysaccharides are produced in 2-gram quantities by chemoenzymatic synthesis (Hyalose LLC, Oklahoma City, Okla.). Methods, both published (20) and patented (U.S. Pat. No. 7,223,571, which is incorporated herein by reference), based on extension of short HA chains (or primers) into much longer HA chains by recombinant *Escherichia coli*-derived HA synthase of *Pasteurella multocida* (PmHAS), will be used. Unlike other HA synthases, PmHAS can elongate exogeneously-supplied short HA chains (e.g. 4 sugars) into longer HA chains (e.g. 5 to 10,000 sugars) (6). The HA oligosaccharide primer synchronizes the non-processive PmHAS polymerization reaction; by synthesizing all the chains in parallel, the final sizes are all very similar or essentially monodisperse (e.g. polydispersity of less than 1.10). To control the size of any polymer preparation, the stoichiometry of the primer to the UDP precursor is adjusted (e.g., more primer will yield many short chains, and conversely, less primer will yield fewer long chains). This method has been performed at the ~0.1-gram scale for the SelectHA™ product line (see http://www.hyalose.com/technology/selectha.html). Larger reaction vessels, solid phase extraction (rather than solvents), and tangential flow filtration (instead of dialysis) are employed in the scale-up process to obtain 2-gram batches. The polymer size is monitored by multi-angle light scattering and agarose gel analyses (20). The HA purity is analyzed by the carbazole assay for HA, Bradford assay (Pierce) for residual protein, and the *Limulus* amebocyte assay (Cambrex) for potential endotoxin. Purity specifications accepted for FDA-approved high molecular weight HA are used in viscoelastic supplementation of the knee as a benchmark. The 2-gram batch size is expected to provide more HA than is needed for the rabbit study (~340 mg each polymer) to allow more thorough analytical testing and to reduce the perceived risk in the manufacturing process.

Determine the Feasibility of Treatment of RA in a Large-Animal Model by Intra-Articular Injection of HA Polysaccharides of a Size Known to Function as an Irreversible HC Acceptor.

A rabbit efficacy study is performed, for example, by a clinical research organization that provides expert regulatory, clinical, and compliance services to medical device and healthcare product manufacturers. A mono-articular model of RA is used. This model induces arthritis in single SJs by locally injecting methylated bovine serum albumin (mBSA) into knee joints of a rabbits that have been previously sensitized to this antigen. This method has been previously described (21) and is known as antigen-induced arthritis (AIA). This method is not rabbit strain dependent, and the percent incidence of arthritis induction is 100%. This mono-articular model has been chosen, as opposed to a systemic RA model, because it is reasonable to expect that the amount of HA polysaccharide required to have an effect on HC-HA in a mono-articular model will be much less than the amount of polysaccharide needed in a systemic model.

Immunization to mBSA:

Rabbits are immunized with 0.5 ml of mBSA homogenized 1:1 with Freund's complete adjuvant at 4 mg/ml. Injections are given subcutaneously at two different sites. Rabbits are subcutaneously boosted with 0.5 ml of the mBSA adjuvant twice weekly for 3 weeks. Two to three weeks after the final boost, serum anti-BSA titers are determined by ELISAs.

Induction of Arthritis:

Knees of mBSA-immunized rabbits are injected intra-articularly under ketamine/xylazine anesthesia. Rabbits receive 500 µl intra-articular injections of mBSA in saline at 2 mg/ml once weekly for 3 weeks. Typically, rabbits develop swelling and redness in mBSA treated joints 7 to 14 days after the third injection of mBSA. This stage of immunized animals (from 7 days after the third injection) is regarded as the pre-arthritic phase of AIA. A standard scoring system, based on swelling and redness of paws, is used for the assessment of the severity of arthritis. The time of appearance of swelling and redness are recorded as the time of onset of arthritis. Joint swelling is scored from 0 to 4 of each knee. During the treatment period, knee (joint) thicknesses at frontal and sagittal planes is measured daily with a micro-caliper (26). Two weeks after the final injection of mBSA, body weights are recorded and the knee joints injected with 500 µl of treatments (HA16K or HA50K) or controls (saline). These injections are repeated once per week for 3 weeks (total of 3 injections per knee; similar to current viscoelastic HA injection protocols).

HA Polysaccharide Treatments:

Typically, about 1 ml of SF accumulates into the inflamed rabbit knee joint with HA concentrations at about 4 mg/ml. In our in vitro studies, adding equivalent amounts of HA polysaccharide that is an irreversible HC acceptor (such as HA16K) to the same amount of HMW HA that is substituted with HCs (i.e. HC-HA) is sufficient to remove >90% HCs from HC-HA. However, in vivo, we expect that LMW HA such as HA16K will diffuse out of the synovial space into the lymphatics, thus possibly requiring larger dosages. Since HA is highly soluble and HA solutions that are 20 mg/ml can be prepared, rabbits are injected with 0.5 ml HA16K or HA50K at 20 mg/ml, once weekly for 3 weeks. This would be expected to provide about 2.5×HA equivalents for HA polysaccharide with respect to the amount of endogenous HA. Thus, approximately 360 mg of HA16K and HA50K is needed to inject 12 knees 3× with 10 mgs/knee.

Harvest of Samples and Data Analysis:

Following the 3 weeks of treatment, blood, SF and tissue are harvested. Knees from all rabbits are fixed in 10% formalin containing 5% cetylpiridinium chloride (to prevent solubilization of HA), decalcified in 5% formic acid, paraffin embedded, and sections processed for routine histology and immunohistochemistry. SF is collected from the knee synovial spaces of sacrificed rabbits using a syringe. Since the amount of SF in the non-inflamed joints of untreated rabbits is small 100 µl), a 400 µl saline lavage is used. Blood is collected from sacrificed rabbits by cardiac puncture. Leukocyte populations are counted on an Advia 120 Hematology analyzer from blood collected by cardiac puncture. Leukocyte populations from pooled SF are counted on a hemocytometer and different leukocyte populations are evaluated by standard histology using Wright-Giemsa staining. The amount of HC-HA present in SF is evaluated by monitoring a molecular weight gel shift of the HCs+/−*Streptomyces* hyaluronidase treatment in a Western blot assay. The regional distribution of HC-HA within the synovial tissue itself is also evaluated by immunohistological co-localization of HC antibodies with the biotinylated HA binding protein.

Example 6

Removal of HCs from Pathological HC-HA Matrices by HA Oligos

Methods have been developed to investigate the parameters by which HA oligos remove HCs from pathological HC-HA matrices to disrupt HA-based leukocyte binding and activation.

Synthesis of Artificial HC-HA:

A method for making artificial HC-HA has been developed using recombinant TSG-6 (rTSG-6) to transfer HCs from purified IαI and a commercial source of HA that is 1000 kDa. This Select HA™ (Hyalose, Inc.) is essentially monodisperse (e.g. polydispersity of 1.007), such that each HA strand is 1000 kDa, contrasted with standard commercial preparations that are highly polydisperse, where HA strands can range from 500 to 1500 kDa. This Select HA is chosen to minimize variable results that might occur between commercial preparations of polydisperse HA. IαI is purified from human serum as described previously (28). Recombinant TSG-6 is prepared as previously described (29), and is also commercially available in both human and mouse forms. Streptavidin-coated 96-well plates, and the biotinylated HA binding protein (HABP) are commercially available and are used to capture HC-HA in each well for leukocyte binding studies (17). In parallel cultures, fluorophore-assisted-carbohydrate-electrophoresis (FACE) is used to quantify the amount of HA bound to each well to prove that the variations seen in leukocyte binding are caused by changes in the numbers of HCs present on HA rather than variations in the amount of HA present in each well. HCs are removed from the HC-HA in the wells of these plates, as described in below. The effect this has on leukocyte adhesion is monitored, as also described below.

Removal of HCs from HC-HA by HA Oligos:

HA oligos eight monosaccharides long (HA8) are used to remove HCs from HC-HA. These oligos are commercially available with a high degree of purity from other oligos. HA8 is the smallest HA oligo that can accept HCs and function as an irreversible HC acceptor. To document the amount of HCs removed by HA8 from HC-HA in the well, HCs are extracted from each well using *Streptomyces* hyaluronidase (that is specific only for HA) and the amount of HCs extracted are measured by Western blot (as shown in FIG. 20).

Specifically, an analysis of heavy chain-hyaluronan complex in mouse proteoglycan-induced arthritis synovial fluid (PGIA SF) is shown (FIG. 20). Evidence is provided for HC transfer onto high molecular weight (HMW) HA in mouse PGIA SF. Both knee (lanes 1-2) and ankle (lanes 3-4) mouse PGIA SF were digested for 24 hours at 37° C. with (+) or without (−) hyaluronidase (Hyase), and analyzed by Western blot analysis probing with a mixture of anti-mouse HC1 and HC2 antibodies. Without hyaluronidase treatment (lanes 1,3), only a pre-IαI band is seen as the HCs, attached to the HMW SF HA (HMW HC-HA) are too large to enter the gel. In lanes 2 and 4, hyaluronidase-released HCs are easily detected in PGIA mouse SF similar to that seen in human RA SF and AIA mouse SF (not shown).

It is expected that HCs below the surface of the HC-HA matrix, and especially the HC-HA that is directly in contact with HABP at the well interface, are unlikely to be removed by the HA oligos, so it would not be expected that that all HCs could be removed from these cultures. Rather, the aim is to use HA oligos to remove enough HCs from HC-HA such that leukocyte adhesion to this HA matrix is significantly diminished. It is expected that prevention of ≥90% of leukocytes from binding to HC-HA could be accomplished. This percentage may be less when HA8 is applied to leukocyte cultures already bound to HC-HA since it is not yet known if HA oligos would be as efficient at displacing bound leukocytes compared to preventing their initial binding to HC-HA.

Synthesis of HC-HA Derived from Synoviocytes:

Human synoviocytes from normal and RA patients are acquired from a commercial source (Cell Applications, Inc.). While it is possible that these cells would spontaneously produce leukocyte-adhesive HA structures, such a phenomenon is uncommon (30) while all other reported cell types require stimulation with a viral mimic, toxins or cytokines to induce the synthesis of leukocyte-adhesive HA structures. Thus, it is expected that cultured synoviocytes would require stimulation to produce HC-HA. Cultured synoviocytes have been shown to produce TSG-6 following TNFα stimulation, which may induce the formation of HC-HA (31). Other stimulants that may induce HC-HA formation are RA-related cytokines, such as IL-1, IL-6, IL-15 and IL-17. The ability of cultured synoviocytes to produce HC-HA in response to these cytokines is tested. If these cytokines fail to induce HC-HA synthesis, the viral mimic poly(I:C) is used. poly(I:C) is well known to induce the formation of leukocyte-adhesive HA structures in cultured cells (2, 32). The relative amount of HCs in the HC-HA structures produced by synoviocytes is confirmed by Western blots of *Streptomyces* hyaluronidase extracts from these cells (as shown in FIG. 20). The effect that addition of rTSG-6 to the culturing media has on promoting the formation of HC-HA by these cells is also tested (as shown in FIG. 19). This procedure is used to: (i) induce synoviocytes to produce HC-HA, (ii) use HA8 to remove the HCs from HC-HA produced by these cells, and (iii) monitor the effect that removal of these HCs from HC-HA has on leukocyte binding. Using similar concentrations and durations of HA8 as learned above, HA8 is used to remove HCs from HC-HA produced by cultured synoviocytes, similar to the procedure described above. This is done both before and after leukocyte adhesion to determine if HA8 can both prevent and disrupt leukocyte binding to HC-HA, respectively. The procedure for leukocyte adhesion is described below.

HC-HA Derived from Human and Mouse SF:

We have shown that SF derived from human patients and mice with RA contain pathological HC-HA (FIG. 20) and that HA oligos can be used to remove almost all of the HCs from this matrix in vitro (FIG. 14). HC-HA derived from the SF of RA patients significantly promoted leukocyte adhesion compared to HA alone (17). This suggests that removal of HCs from HC-HA by irreversible transfer to HA oligos should have a similar effect at reducing leukocyte adhesion to SF-derived HA. Accordingly, in this method HA8 is used remove HCs from SF-derived HC-HA, before and after leukocyte adhesion, to evaluate the effect it has to prevent and disrupt leukocyte adhesion to this pathological matrix. This assay is performed essentially as described previously (17), where HC-HA from the SF of human patients and mice with RA is captured on HABP-coated plates, identical to the procedure described for artificially created HC-HA above. HCs are removed from the HC-HA in the wells of these plates, as described above. The effect this has on leukocyte adhesion is monitored as described below.

Leukocyte Adhesion Assay:

The monocytic U937 cell line is used for initial leukocyte binding studies since this cell line readily binds HC-HA (FIG. 19) (33) and demonstrates CD44 capping, indicative of activation, when bound to HA cables. These cells are fluorescently labeled with Dil (a lipophilic membrane stain) and the number of U937 cells bound to HC-HA is determined by comparing the relative intensity of *Streptomyces* hyaluronidase extracted cells to a known number of fluorescently labeled U937 cells on a fluorometer (FIG. 19). From previous studies (not shown), we know that 2 million U937 cells per/ml, adding 1 ml for every 4 $cm^2$ of surface, area is ideal. This concentration provides an adequate monolayer of U937 cells to cover the entire surface area of the well.

Adhesion of different Leukocyte Populations to HC-HA:

Nothing is known regarding the ability of HC-HA to promote the accumulation of distinct leukocyte populations in the inflamed joint. Our hypothesis is that not all leukocyte populations bind HC-HA with equal avidity. A method to investigate this hypothesis, by monitoring the effect disruption of HC-HA has on the accumulation of different leukocyte populations in SF and the inflamed joint tissue, is as follows. Mixed leukocyte populations, derived from whole blood, are applied to artificial HC-HA, HC-HA produced by synoviocytes, and HC-HA derived from human patients and mice with RA. Flow-cytometry is used to measure the relative percentages of leukocytes that bind to HC-HA, comparing these percentages to the percentages of leukocytes originally applied to HC-HA. Mixed leukocyte populations are purified from whole mouse and human blood using the "buffy coat" procedure of density gradient centrifugation. The relative percentage of leukocytes in human blood is 4-6% monocytes, 50-70% neutrophils, 25-35% lymphocytes, 1-3% eosinophils, and 0.4-1% basophils. The mixed population of leukocytes is allowed to bind HC-HA by allowing them to settle, by gravity, onto HC-HA under static conditions (30 min). Unbound leukocytes are removed from HC-HA bound cells by washing and are saved in a separate tube as the unbound fraction. Bound cells are released from HC-HA by a 5 min treatment with *Streptomyces* hyaluronidase and saved in a separate tube as the bound fraction. To determine the relative percentages of leukocyte populations that preferentially bind HC-HA, (i) an aliquot of the leukocytes originally applied to HC-HA is compared to (ii) the unbound fraction, and (iii) the bound fraction.

Leukocyte Activation by HC-HA: We showed that monocytic leukocytes (U937 cells) demonstrate signs of activation when bound to leukocyte-adhesive HA structures produced by gut smooth muscle cells, including "capping" of the HA receptor CD44 on their cell surface and subsequent digestion of the pathological HA matrix. Nothing is known regarding the effect that leukocyte engagement of HC-HA has on the induction of pro-inflammatory cytokines and chemokines. Our hypothesis is that leukocytes bound to HC-HA are stimulated to produce an array of inflammatory mediators that regulate inflammation in the joint. A method to evaluate the gene expression and protein levels of several cytokines and chemokines produced by mixed populations of leukocytes bound to artificial HC-HA, HC-HA produced from cultured synoviocytes, and HC-HA from human and mouse SF, is as follows. Mixed populations of leukocytes from human and mouse blood are isolated and allowed to bind HC-HA, washing away unbound leukocytes. The leukocytes are incubated at 37° C. in the presence of HC-HA for 2, 4, 6, and 12 hours. A portion of leukocytes not applied to HC-HA, and the portion of leukocytes that are applied to HC-HA but do not bind to it, are also incubated at the same temperature and time points to serve as negative controls. Positive controls include input, bound, and unbound fractions treated with lipopolysaccharide. Cytokine and chemokine gene expression are evaluated by quantitative real-time PCR and protein levels are monitored by flow-cytometry using commercially available kits (BD Biosciences), including the cytokines IL-8, IL-1β, IL-6, IL-10, TNF, IL-12p70 and the chemokines IL-8, RANTES, IFNγ, □MCP-1 and IP10. If mixed populations of leukocytes demonstrate an induction in these inflammatory mediators, HA oligos are used to remove HCs from the HC-HA matrices (as described above) and the effect this has on preventing this induction is evaluated. Furthermore, if mixed populations of leukocytes show changes in cytokine and/or chemokine production, flow-cytometry is used to isolate individual leukocyte populations, they are allowed to bind HC-HA, and the effect this interaction has on the cytokine and chemokine production by these individual leukocyte populations is examined.

Example 7

Figure 14:
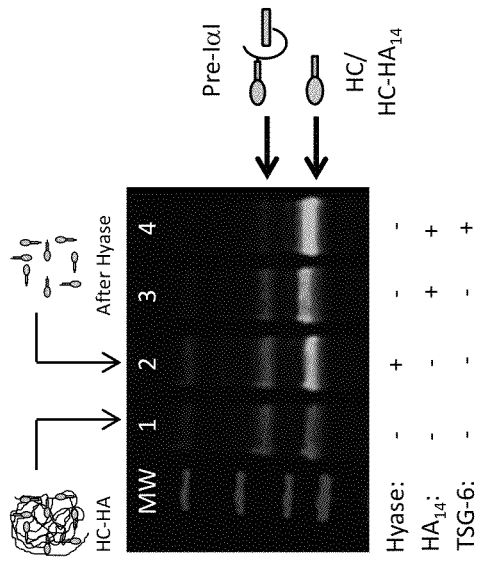
FIG. 14 shows results of irreversible transfer of heavy chains from mouse synovial fluid hyaluronan to hyaluronan oligosaccharides, by Western blot.
Figure 15:
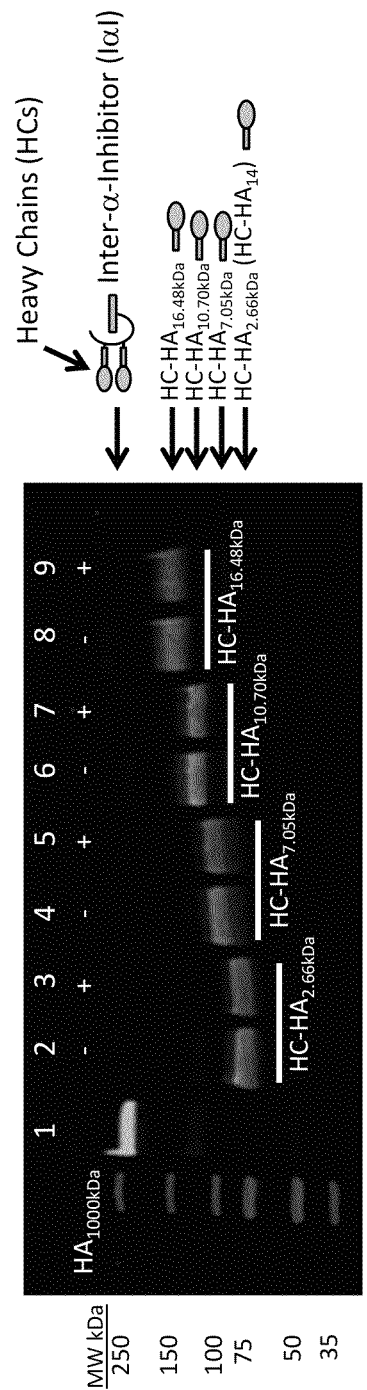
FIG. 15 shows results of a size-range study of irreversible heavy-chain transfer, by Western blot.
Figure 16:
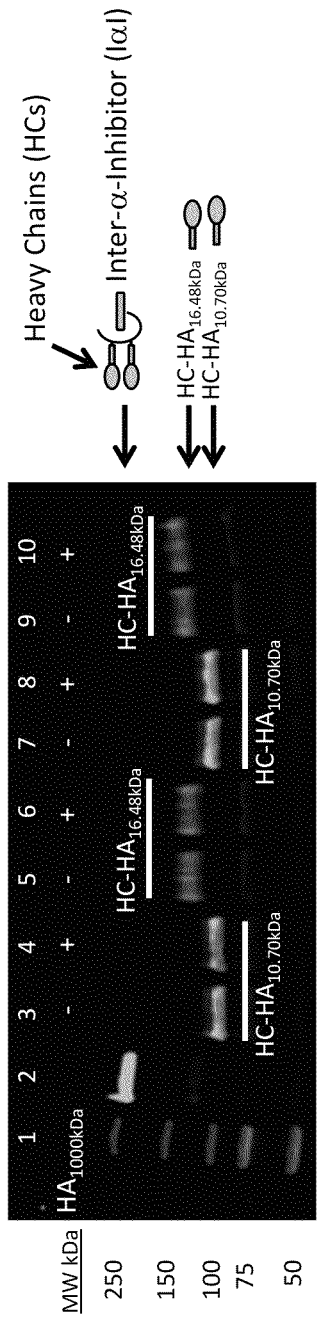
FIG. 16 shows results of another size-range study of irreversible heavy-chain transfer, by Western blot.
Figure 17:
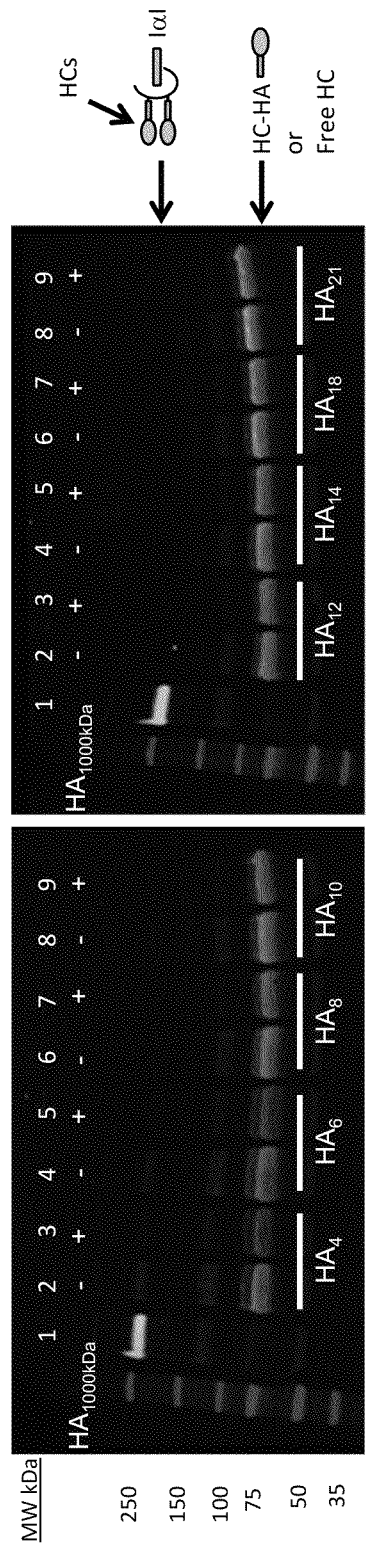
FIG. 17 shows results of another size-range study of irreversible heavy-chain transfer, by Western blot.

Evaluating the Effect of Disruption of Abnormal Matrix by Administration of HA Oligos A method for evaluating the effect of disruption of abnormal matrix by administration of HA oligos is as follows. Normal mice are subjected to mono-articular RA to allow HC-HA to form in the SF of inflamed joints. Subsequently, the ability of HA8 to remove HCs from HC-HA matrices in SF is monitored and the effect this has on the accumulation and activation of leukocytes is evaluated. HA8 is labeled with Alexa Fluor 594 (red) and 488 (green) hydrazine (Molecular Probes, Inc.) for ease of tracking and quantification. These fluorophores attach to the reducing terminus of the oligo, such that there is one fluorophore per HA oligo to permit quantitative and linear measurements of the oligo. The labeled oligos are purified using Sephadex G-50 and their functionality as an irreversible HC-acceptor is tested with non-labeled HA8 as a positive control. In the unlikely event that the fluorophores compromise the ability of the HA8 to function as an irreversible HC acceptor, a suitable replacement fluorophore would be identified and/or a slightly longer HA oligo than HA8 that might circumvent this adverse side effect would be chosen. The route of administration for recombinant F-HA8 is intravenous, using (i) a catheter in the jugular vein, preinstalled by Jackson Laboratories, and/or (ii) an osmotic pump, pre-implanted by Jackson Laboratories. It is expected that the modestly higher cost of these pre-installed catheters and pumps will be offset by the reproducibility of the repeated injections, and blood draws, that will be required for such a study. A single 100 µl intravenous injection of doses ranging from 1-10 mg/ml is made. The intravenous osmotic pump is also tested at similar concentrations. Circulating levels of F-HA8 are measured by drawing 25-50 µl of blood from the intravenous catheter 2, 4, 6 and 12 hrs after the initial injection, followed by daily draws, if necessary, until F-HA8 levels drop below the level of detection. Urine is collected by picking up the mice by the skin of their neck and letting them urinate onto a piece of Parafilm™, after which the urine is transferred to a tube using a pipet. Oligo levels are quantified by measuring an aliquot of serum and urine in a fluorometer, comparing the signal to known standards of F-HA8. It is expected that the best dose, and route of administration, to reach oligo blood levels of 0.1 mg/ml over a period of 2-4 days can thereby be determined. These metrics are based on calculations from in vitro dose-response and kinetic studies of HC swapping from HC-HA onto HA oligos (not shown). Although the addition of recombinant TSG-6 accelerated the removal of HCs from HC-HA, endogenous levels of TSG-6 were sufficient to remove about half of the HCs in 72 hrs (FIG. 14). Thus, it is expected that endogenous TSG-6 should be sufficient to deplete HC-HA within 2-4 days. The effect that intravenous injections of recombinant TSG-6 have in accelerating this process is also tested (similar to the intravenous injections of TSG-6 described in (29)). Once the optimum route of delivery and dosing to achieve these circulating HA8 levels are determined, Balb/C mice are subjected to a mono-articular model of RA. The oligos are injected before and after the onset of inflammation, and the effects that HA8 has on levels, activity, and distribution of TSG-6, HA, and HC-HA and on counts and populations of leukocytes are determined. Specifically, the oligos are injected (i) at the same time as the intra-articular injections of mBSA (before the onset of inflammation), or (ii) seven days after the intra-articular injection of mBSA (after the onset of inflammation). The effect that these two approaches have on the formation or disruption of HC-HA and the subsequent effect this has on the accumulation and activation of leukocytes in the inflamed joint are documented.

Example 8

Another example embodiment relates to the controlled and extended release of the LMW HA oligosaccharides in tissues through encapsulation in tyramine-based (TB) HA hydrogels.

We have determined that tyramine-substituted (TS) HA can be modified with HC in vitro via recombinant TSG-6 and serum as a source of IαI similar to "naked" HA (FIG. 9). Specifically, results from Western blots demonstrate that HCs from IαI were transferred to a commercial source of HA (panels A,C) and T-HA (panels B,D) via enzymatic transfer by TSG-6. By systematically (1:4) decreasing the amount of HA in the reaction mixture while keeping the amount of the HC donor, IαI, in serum and TSG-6 concentration constant, we have created HC-HA complexes which vary in HC density on the HA backbone. The HA-bound HC have such a large combined molecular weight (>1700 kDa) that they are unable to enter the gel (panels C,D). Hyaluronidase treatment (panels A,B) releases the ~75 kDa HC from the large HA molecule, permitting them to run as a distinct band on an SDS-PAGE gel.

The resulting HC-TS-HA can be subsequently cross-linked with horseradish peroxidase and hydrogen peroxide to form HC-TB-HA hydrogels (data not shown). These HC-TB-HA hydrogels can be used for various tissue engineering and repair applications with them engineered to be patient-specific through the use of a patient's own serum as the source of IαI.

With respect to the new combinatorial materials described herein, HC-TS-HA, which refers to hyaluronan (HA) chains substituted with both heavy chains (HC) from IαI and tyramine, and HC-TB-HA hydrogels, which refers to hydrogels formed from HC-TS-HA chains as a result of dityramine formation, it appears that the transfer of heavy chains from IαI by TSG-6 to already cross-linked TB-HA hydrogels occurs only at the surface of the hydrogel mass. Cross-linking doesn't occur within the hydrogel mass as both the TSG-6 and/or IαI are too large to enter the hydrogel pores.

By virtue of the spacing of tyramine adducts on TS-HA chains, e.g. one tyramine every 20 repeat disaccharides (or HA40), the size of the intervening stretches of HA oligosaccharide between tyramine adducts (HA39) may function similar to LMW HA, which serve as acceptors for HC swapping, but not as donors (i.e. irreversible acceptors of HC). Currently, HA molecules ranging from 8-14 monosaccharides in length have been found functional in the disclosed methods, although it is believed that HA molecules of greater length, e.g. to less than about 160 monosaccharides, more preferably to 40 monosaccharides would also work to serve as LMW HA to achieve irreversible HC attachment via TSG-6. Regardless of the upper bound for LMW HA useful in the disclosed methods, TS-HA, unlike native or naked HA, may be a form of high molecular weight (HMW) HA, that is an irreversible acceptor of HC similar to the low molecular weight (LMW) HA oligosaccharides that are the focus of this disclosure.

Similar to the point above, the spacing of the tyramine adducts on TS-HA chains, e.g. one tyramine every 20 repeat disaccharides (or HA40), generates upon hyaluronidase digestion oligosaccharides that are predicted to be in the size range of those LMW HA oligosaccharides that serve as acceptors for HC swapping, but not as donors (i.e. irreversible acceptors of HC) similar to the LMW HA oligosaccharides that are the focus of this invention.

Based on the work by Kim et al (34) it appears that uncross-linked TS-HA alone when injected into an RA joint in an RA animal model is able to successfully treat the RA. The authors postulate that the therapeutic effect is derived from the ability of the TS-HA chains to scavenge oxygen free radicals known to be present in RA joints and previously shown to cross-link TS-HA chains into TB-HA hydrogels in the absence of HRP or hydrogen peroxide. However, in light of the observations described above, it is expected instead that the therapeutic effect of the TS-HA chains is that the TS-HA, either as HMW TS-HA chains or upon fragmentation by free radicals or the action of hyaluronidase to HA oligosaccharides, serve as a source of irreversible HC acceptors to remove HC from endogenous synovial fluid HA and thus remove the binding and activation signal for inflammatory cells that perpetuates the disease.

One embodiment for treatment (whether injectable, inhalable, digestible, topical, etc.) of an inflammatory condition is encapsulation of naked LMW HA oligosaccharides (that can serves as acceptors for HC swapping, but not as donors) within TB-HA hydrogels designed to extend the release of the naked HA oligosaccharides over a 30 day or other desirable period similar to the previously reported in vivo release of dexamethasone. This therapeutic release of naked HA oligosaccharides would be responsible for the initial removal of HCs from the synovial fluid HMW HA and relief from symptoms (and possibly disease). Then the slow degradation of the TB-HA hydrogel would provide for release of TS-HA oligosaccharides as irreversible HC acceptors over a longer time period so as to extend the relief from symptoms (and possibly disease) perhaps out 3-12 months. In this manner, a novel therapy would be available to provide a treatment that provides relief from chronic inflammation that does not act by directly altering immune cell function and thus produce associated complications, and is either simple to administer frequently (i.e. through a topical lotion, ingestion of a pill, an inhaler) or administer occasionally only every 3, 6 or 12 months (i.e. transfusion, intra-articular injection) as a minimally invasive, outpatient procedure.

Example 9

Another example embodiment is intra-articular injection of LMW HA encapsulated in TB-HA hydrogel into the joints of rheumatoid arthritis patients. The hydrogel can be engineered to release the LMW HA over a specified time period (e.g. 1 month) at therapeutic levels required to transfer endogenous HC from synovial fluid HA to the LMW HA. This is accomplished through endogenous TSG-6 already present in the synovial fluid. The LMW HC-HA is subsequently cleared rapidly from the joint space removing the signal responsible for binding and activation of inflammatory cells thus reducing the signs and symptoms of the disease, and ultimately helping slow or halt progression of further tissue damage in the joint. Our experiments (FIG. 9) show that TSG-6 does transfer HC to (TS) HA. However, it does not transfer HC once the (TS) HA is first cross-linked to form a hydrogel (data not shown). Thus the hydrogel acts as an inert carrier until it is eventually degraded. Its degradation is predicted to result in formation of HA and (TS) HA oligosaccharides with sufficiently small size to be unable to serve as a donor for HC transfer thus augmenting the encapsulated LMW HA.

The foregoing experiments have confirmed: 1) the irreversible nature of the transfer of HC from HMW HA to LMW HA using recombinant TSG-6; 2) the ability to transfer HC ligands from HA of synovial fluid of rheumatoid arthritis patients to LMW HA using recombinant TSG-6; and 3) the ability to transfer HC from serum IαI to TS-HA using recombinant TSG-6 and subsequently form HC-TB-HA hydrogels via cross-linking with peroxidase and hydrogen peroxide.

BIBLIOGRAPHY AND REFERENCES CITED

1. Castor C W, Prince R K, Hazelton M J. Hyaluronic acid in human synovial effusions; a sensitive indicator of altered connective tissue cell function during inflammation. Arthritis Rheum. 1966; 9(6):783-94.
2. de la Motte C A, Hascall V C, Drazba J, Bandyopadhyay S K, Strong S A. Mononuclear leukocytes bind to specific hyaluronan structures on colon mucosal smooth muscle cells treated with polyinosinic acid:polycytidylic acid: inter-alpha-trypsin inhibitor is crucial to structure and function. Am J. Pathol. 2003; 163(1):121-33.
3. Brown T J, Laurent U B, Fraser J R. Turnover of hyaluronan in synovial joints: elimination of labelled hyaluronan from the knee joint of the rabbit. Exp Physiol. 1991; 76(1):125-34.
4. Hascall V C, and Laurent, T. C. Science of Hyaluronan Today. In: Hascall V C, and Yanagishita, M. eds, editor: Seikagaku Corp., Tokyo, Japan; 1997.

5. Decker B, Mc G W, Mc K B, Slocumb C H. Concentration of hyaluronic acid in synovial fluid. Clin Chem. 1959; 5:465-9.
6. Sandson J, Hamerman D, Schwick G. Altered properties of pathological hyaluronate due to a bound inter-alpha trypsin inhibitor. Trans Assoc Am Physicians. 1965; 78:304-13.
7. Zhao M, Yoneda M, Ohashi Y, Kurono S, Iwata H, Ohnuki Y, et al. Evidence for the covalent binding of SHAP, heavy chains of inter-alpha-trypsin inhibitor, to hyaluronan. J Biol. Chem. 1995; 270(44):26657-63.
8. Fries E, Kaczmarczyk A. Inter-alpha-inhibitor, hyaluronan and inflammation. Acta Biochim Pol. 2003; 50(3):735-42.
9. Milner C M, Tongsoongnoen W, Rugg M S, Day A J. The molecular basis of inter-alpha-inhibitor heavy chain transfer on to hyaluronan. Biochem Soc Trans. 2007; 35(Pt 4):672-6.
10. Wisniewski H G, Vilcek J. Cytokine-induced gene expression at the crossroads of innate immunity, inflammation and fertility: TSG-6 and PTX3/TSG-14. Cytokine Growth Factor Rev. 2004; 15(2-3):129-46.
11. Mukhopadhyay D, Hascall V C, Day A J, Salustri A, Fulop C. Two distinct populations of tumor necrosis factor-stimulated gene-6 protein in the extracellular matrix of expanded mouse cumulus cell-oocyte complexes. Arch Biochem Biophys. 2001; 394(2):173-81.
12. Fulop C, Szanto S, Mukhopadhyay D, Bardos T, Kamath R V, Rugg M S, et al. Impaired cumulus mucification and female sterility in tumor necrosis factor-induced protein-6 deficient mice. Development. 2003; 130(10):2253-61.
13. Mukhopadhyay D, Asari A, Rugg M S, Day A J, Fulop C. Specificity of the tumor necrosis factor-induced protein 6-mediated heavy chain transfer from inter-alpha-trypsin inhibitor to hyaluronan: implications for the assembly of the cumulus extracellular matrix. J Biol. Chem. 2004; 279 (12):11119-28.
14. Jessen T E, Odum L. Role of tumour necrosis factor stimulated gene 6 (TSG-6) in the coupling of inter-alpha-trypsin inhibitor to hyaluronan in human follicular fluid. Reproduction. 2003; 125(1):27-31.
15. Forteza R, Casalino-Matsuda, S., Monon-Medina, M. E., Rugg, M. S., Milner, C. M. and Day, A. J. TSG-6 Potentiates the Antitissue Kallikrein Activity of Inter-alpha-inhibitor through Bikunin Release. Am J Respir Cell Mol Biol. 2007; 36:20-31.
16. Al'Qteishat A, Gaffney J, Krupinski J, Rubio F, West D, Kumar S, et al. Changes in hyaluronan production and metabolism following ischaemic stroke in man. Brain. 2006; 129(Pt 8):2158-76.
17. Zhuo L, Kanamori A, Kannagi R, Itano N, Wu J, Hamaguchi M, et al. SHAP potentiates the CD44-mediated leukocyte adhesion to the hyaluronan substratum. J Biol. Chem. 2006; 281(29):20303-14.
18. Stern R, Kogan G, Jedrzejas M J, Soltes L. The many ways to cleave hyaluronan. Biotechnol Adv. 2007; 25(6):537-57.
19. Levick J R, McDonald J N. Fluid movement across synovium in healthy joints: role of synovial fluid macromolecules. Ann Rheum Dis. 1995; 54(5):417-23. PMCID: 1005608.
20. Fraser J R, Laurent T C. Turnover and metabolism of hyaluronan. Ciba Found Symp. 1989; 143:41-53; discussion-9, 281-5.
21. Coleman P J, Scott D, Mason R M, Levick J R. Role of hyaluronan chain length in buffering interstitial flow across synovium in rabbits. J Physiol. 2000; 526 Pt 2: 425-34. PMCID: 2270008.
22. Coleman P J, Scott D, Ray J, Mason R M, Levick J R. Hyaluronan secretion into the synovial cavity of rabbit knees and comparison with albumin turnover. J Physiol. 1997; 503 (Pt 3):645-56. PMCID: 1159848.
23. Lindenhayn K, Heilmann H H, Niederhausen T, Walther H U, Pohlenz K. Elimination of tritium-labelled hyaluronic acid from normal and osteoarthritic rabbit knee joints. Eur J Clin Chem Clin Biochem. 1997; 35(5):355-63.
24. Fraser J R, Kimpton W G, Pierscionek B K, Cahill R N. The kinetics of hyaluronan in normal and acutely inflamed synovial joints: observations with experimental arthritis in sheep. Semin Arthritis Rheum. 1993; 22(6 Suppl 1):9-17.
25. Glant T T, Finnegan A, Mikecz K. Proteoglycan-induced arthritis: immune regulation, cellular mechanisms, and genetics. Crit Rev Immunol. 2003; 23(3):199-250.
26. Calabro A, Benavides M, Tammi M, Hascall V C, Midura R J. Microanalysis of enzyme digests of hyaluronan and chondroitin/dermatan sulfate by fluorophore-assisted carbohydrate electrophoresis (FACE). Glycobiology. 2000; 10(3):273-81.
27. Sanggaard K W, Scavenius C, Rasmussen A J, Wisniewski H G, Thøgersen I B, Enghild J J. The TSG-6/hc2-mediated transfer is a dynamic process shuffling heavy chains between glycosaminoglycans. J Biol Chem 2010, Jul. 16; 285(29):21988-93.
28. Wisniewski H G, Burgess W H, Oppenheim J D, Vilcek J. TSG-6, an arthritis-associated hyaluronan binding protein, forms a stable complex with the serum protein inter-alpha-inhibitor. Biochemistry 1994, Jun. 14; 33(23):7423-9.
29. Bárdos T, Kamath R V, Mikecz K, Glant T T. Anti-Inflammatory and chondroprotective effect of TSG-6 (tumor necrosis factor-alpha-stimulated gene-6) in murine models of experimental arthritis. Am J Pathol 2001, November; 159(5):1711-21.
30. Aytekin M, Comhair S A, de la Motte C, Bandyopadhyay S K, Farver C F, Hascall V C, et al. High levels of hyaluronan in idiopathic pulmonary arterial hypertension. Am J Physiol Lung Cell Mol Physiol 2008, November; 295(5): L789-99.
31. Wisniewski H G, Maier R, Lotz M, Lee S, Klampfer L, Lee T H, Vilcek J. TSG-6: A TNF-, IL-1-, and lps-inducible secreted glycoprotein associated with arthritis. J Immunol 1993, Dec. 1; 151(11):6593-601.
32. Lauer M E, Mukhopadhyay D, Fulop C, de la Motte C A, Majors A K, Hascall V C. Primary murine airway smooth muscle cells exposed to poly(I,C) or tunicamycin synthesize a leukocyte-adhesive hyaluronan matrix. J Biol Chem 2009, Feb. 20; 284(8):5299-312.
33. de La Motte C A, Hascall V C, Calabro A, Yen-Lieberman B, Strong SA. Mononuclear leukocytes preferentially bind via CD44 to hyaluronan on human intestinal mucosal smooth muscle cells after virus infection or treatment with poly(I.C). J Biol Chem 1999, Oct. 22; 274(43):30747-55.
34. Kim K S, Park S J, Yang J A, Jeon J H, Bhang S H, Kim B S, Hahn S K. Injectable hyaluronic acid-tyramine hydrogels for the treatment of rheumatoid arthritis. Acta Biomater. 2011, February; 7(2):666-74.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A method of transferring Inter-α-Inhibitor (IαI) heavy chains (HCs) from high molecular weight (HMW) hyaluronic acid (HA) to low molecular weight (LMW) hyaluronic acid (HA), within a site of inflammation caused by asthma in an individual in need thereof, comprising administering to the site:

a) a LMW HA compound comprising the hyaluronan-containing structure of:

[chemical structure]

wherein:
A is hydrogen;
B is hydroxyl;
x=0 or 1;
y=0 or 1; and
n=3 to 70, with the proviso that if n=3, then at least one of x and y=1 and b) a protein selected from the group consisting of mammalian TSG-6 protein, recombinant mammalian TSG-6 protein, human TSG-6 protein, and recombinant human TSG-6 protein, in amounts of a) and b) effective to transfer the IαI HCs from the HMW HA to the LMW HA compound.

2. The method of claim 1, wherein the individual is a mammal selected from the group consisting of a human, a dog, a cat, and a horse.

3. The method of claim 1, wherein n=3 to 45.

4. The method of claim 1, wherein x, n, and y are selected from the group consisting of: (i) x=0, n=4, and y=0; (ii) x=0, n=5, and y=0; (iii) x=0, n=6, and y=0; (iv) x=0, n=7, and y=0; (v) x=0, n=9, and y=0; (vi) x=1, n=10, and y=0; and (vii) x=0, n=10, and y=1.

5. The method of claim 1, wherein x, n, and y are selected from the group consisting of: (i) x=0, n=43, and y=0; (ii) x=1, n=43, and y=0; (iii) x=0, n=43, and y=1; (iv) x=1, n=43, and y=1; and (v) x=0, n=44, and y=0.

* * * * *

UNITED STATES PATENT AND TRADEMARK OFFICE
CERTIFICATE OF CORRECTION

PATENT NO.         : 9,012,395 B2                                                Page 1 of 1
APPLICATION NO.    : 14/159129
DATED              : April 21, 2015
INVENTOR(S)        : Anthony Calabro, Mark Lauer and Vincent Hascall It is certified that error appears in the above-identified patent and that said Letters Patent is hereby corrected as shown below:

In the Specification

Column 32, line 17, the text "100 µl)" should read --(≤ 100 µl)--.

Signed and Sealed this
Twenty-fifth Day of August, 2015

Michelle K. Lee
*Director of the United States Patent and Trademark Office*